(12) United States Patent
Udrea et al.

(10) Patent No.: US 11,073,415 B2
(45) Date of Patent: Jul. 27, 2021

(54) THERMAL FLUID FLOW SENSOR HAVING A DIELECTRIC MEMBRANE COMPRISING DISCONTINUITIES BETWEEN THE HEATING ELEMENT AND AN EDGE

(71) Applicant: Flusso Limited, Cambridge (GB)

(72) Inventors: Florin Udrea, Cambridge (GB); Andrea De Luca, Cambridge (GB); Claudio Falco, Cambridge (GB); Ethan Gardner, Kineton (GB); Syed Zeeshan Ali, Cambridge (GB)

(73) Assignee: FLUSSO LIMITED, Cambridge (GB)

( * ) Notice: Subject to any disclaimer, the term of this patent is extended or adjusted under 35 U.S.C. 154(b) by 0 days.

(21) Appl. No.: 16/658,711

(22) Filed: Oct. 21, 2019

(65) Prior Publication Data

US 2021/0116281 A1    Apr. 22, 2021

(51) Int. Cl.
| | |
|---|---|
| *G01F 1/68* | (2006.01) |
| *G01F 1/688* | (2006.01) |
| *G01F 1/708* | (2006.01) |
| *G01F 1/69* | (2006.01) |
| G01F 15/02 | (2006.01) |
| G01F 1/698 | (2006.01) |

(52) U.S. Cl.
CPC .............. *G01F 1/6888* (2013.01); *G01F 1/69* (2013.01); *G01F 1/7084* (2013.01); *G01F 1/698* (2013.01); *G01F 15/022* (2013.01)

(58) Field of Classification Search
None
See application file for complete search history.

(56) References Cited

U.S. PATENT DOCUMENTS

| | | | | |
|---|---|---|---|---|
| 3,992,940 A | | 11/1976 | Platzer, Jr. | |
| 4,944,035 A | * | 7/1990 | Aagardl | G01N 25/005 |
| | | | | 374/30 |
| 5,321,983 A | * | 6/1994 | Nagata | G01F 1/698 |
| 5,804,720 A | * | 9/1998 | Morimasa | G01F 1/6845 |
| | | | | 73/204.23 |
| 6,019,505 A | * | 2/2000 | Bonne | G01N 27/18 |
| | | | | 374/40 |

(Continued)

FOREIGN PATENT DOCUMENTS

| | | |
|---|---|---|
| DE | 9919398 A1 | 5/2000 |
| EP | 2157411 A1 | 2/2010 |

(Continued)

OTHER PUBLICATIONS

B. Van Oudheusden, "Silicon flow sensors," in Control Theory and Applications, IEE Proceedings D, 1988, pp. 373-380.

(Continued)

*Primary Examiner* — Harshad R Patel
(74) *Attorney, Agent, or Firm* — Tucker Ellis LLP

(57) ABSTRACT

We disclose herein a flow and thermal conductivity sensor comprising a semiconductor substrate comprising an etched portion, a dielectric region located on the semiconductor substrate, wherein the dielectric region comprises at least one dielectric membrane located over the etched portion of the semiconductor substrate and a heating element located within the dielectric membrane. The dielectric membrane comprises one or more discontinuities located between the heating element and an edge of the dielectric membrane.

19 Claims, 19 Drawing Sheets

(56) References Cited

U.S. PATENT DOCUMENTS

| | | | | |
|---|---|---|---|---|
| 6,046,398 | A * | 4/2000 | Foote | G01J 5/02 374/178 |
| 6,460,411 | B1 * | 10/2002 | Kersjes | G01F 1/6845 73/204.26 |
| 2002/0100316 | A1 * | 8/2002 | James | G01F 1/6845 73/204.26 |
| 2003/0041664 | A1 * | 3/2003 | Ariyoshi | G01F 1/696 73/204.26 |
| 2007/0011867 | A1 * | 1/2007 | Yao | G01F 1/6845 29/611 |
| 2007/0017285 | A1 * | 1/2007 | Wang | G01F 1/68 73/204.26 |
| 2007/0113644 | A1 * | 5/2007 | Manaka | G01N 25/66 73/204.26 |
| 2007/0204688 | A1 * | 9/2007 | Dmytriw | G01F 1/688 73/204.26 |
| 2009/0016403 | A1 * | 1/2009 | Chen | G01F 1/6845 374/45 |
| 2009/0158859 | A1 * | 6/2009 | Huang | G01F 1/6845 73/861.351 |
| 2009/0164163 | A1 * | 6/2009 | Wang | G01F 1/6965 702/100 |
| 2010/0078753 | A1 * | 4/2010 | Mehregany | G01F 1/6888 257/467 |
| 2010/0175468 | A1 * | 7/2010 | Anzai | G01F 1/6842 73/202 |
| 2011/0030468 | A1 * | 2/2011 | Chen | G01F 1/6845 73/204.26 |
| 2011/0211613 | A1 * | 9/2011 | Herrmann | G01J 5/02 374/178 |
| 2012/0216629 | A1 * | 8/2012 | Huang | G01F 1/7084 73/861.95 |
| 2014/0190251 | A1 * | 7/2014 | Huang | G01F 1/692 73/204.24 |
| 2014/0190252 | A1 * | 7/2014 | Huang | G01F 1/6845 73/204.25 |
| 2016/0025660 | A1 * | 1/2016 | Hepp | G01F 1/692 73/25.05 |
| 2016/0195419 | A1 * | 7/2016 | Hepp | G01F 1/6845 73/204.23 |
| 2016/0216144 | A1 | 7/2016 | Figi et al. | |
| 2018/0143051 | A1 | 5/2018 | Bentley et al. | |
| 2018/0306621 | A1 * | 10/2018 | Hornung | G01F 1/6847 |
| 2019/0301906 | A1 * | 10/2019 | Udrea | G01F 1/698 |
| 2019/0301909 | A1 * | 10/2019 | Nakano | G01F 1/698 |

FOREIGN PATENT DOCUMENTS

| | | |
|---|---|---|
| EP | 3392621 A1 | 10/2018 |
| WO | 9836247 A1 | 8/1998 |
| WO | 2014102086 A1 | 7/2014 |

OTHER PUBLICATIONS

B. Van Oudheusden, "Silicon thermal flow sensors," Sensors and Actuators A: Physical, vol. 30, pp. 5-26, 1992.

N. Nguyen, "Micromachined flow sensors—A review," Flow measurement and Instrumentation, vol. 8, pp. 7-16, 1997.

Y.-H. Wang et al., "Mems-based gas flow sensors," Microfluidics and nanofluidics, vol. 6, pp. 333-346, 2009.

J. T. Kuo et al., "Micromachined Thermal Flow Sensors'A Review," Micromachines, vol. 3, pp. 550-573, 2012.

A. Van Putten and S. Middelhoek, "Integrated silicon anemometer," Electronics Letters, vol. 10, pp. 425-426, 1974.

A. Van Putten, "An integrated silicon double bridge anemometer," Sensors and Actuators, vol. 4, pp. 387-396, 1983.

B. Van Oudheusden and J. Huijsing, "Integrated flow friction sensor," Sensors and Actuators, vol. 15, pp. 135-144, 1988.

J. H. Huijsing et al., "Monolithic integrated direction-sensitive flow sensor," Electron Devices, IEEE Transactions on, vol. 29, pp. 133-136, 1982.

W. S. Kuklinski et al., "Integrated-circuit bipolar transistor array for fluid-velocity measurements," Medical and Biological Engineering and Computing, vol. 19, pp. 662-664, 1981.

T. Qin-Yi and H. Jin-Biao, "A novel Cmos flow sensor with constant chip temperature (CCT) operation," Sensors and actuators, vol. 12, pp. 9-21, 1987.

D. Moser et al., "Silicon gas flow sensors using industrial CMOS and bipolar IC technology," Sensors and Actuators A: Physical, vol. 27, pp. 577-581, 1991.

L. Lofdahl et al., "A sensor based on silicon technology for turbulence measurements," Journal of Physics E: Scientific Instruments, vol. 22, p. 391, 1989.

R. Kersjes et al., "An integrated sensor for invasive blood-velocity measurement," Sensors and Actuators A: Physical, vol. 37, pp. 674-678, 1993.

A. Van der Wiel et al.,"A liquid velocity sensor based on the hot-wire principle," Sensors and Actuators A: Physical, vol. 37, pp. 693-697, 1993.

E. Yoon and K. D. Wise, "An integrated mass flow sensor with on-chip CMOS interface circuitry," Electron Devices, IEEE Transactions on, vol. 39, pp. 1376-1386, 1992.

N. Sabaté et al., "Multi-range silicon micromachined flow sensor," Sensors and Actuators A: Physical, vol. 110, pp. 282-288, 2004.

G. De Graaf et al., "Surface-micromachined thermal conductivity detectors for gas sensing", ResearchGate, IEEE Instrumentation and Measurement Technology Conference, May 2012.

International Search Report and Written Opinion from corresponding International Application No. PCT/EP2020/079575, dated Jan. 22, 2021, 14 pages.

* cited by examiner

THERMAL FLUID FLOW SENSOR HAVING A DIELECTRIC MEMBRANE COMPRISING DISCONTINUITIES BETWEEN THE HEATING ELEMENT AND AN EDGE

FIELD OF THE DISCLOSURE

This present disclosure relates to a micro-machined sensor, particularly but not exclusively, the disclosure relates to a fluid flow sensor having a heater formed within a discontinuous dielectric membrane for sensing properties of a fluid flow or components of a fluid based on thermal conductivity properties.

BACKGROUND

Thermal fluid flow sensors utilise the thermal interaction between the sensor itself and the fluid. Depending upon the physical phenomena governing the interaction, flow sensors can be classified into the following three categories:
 (i) anemometric sensors that measure the convective heat transfer induced by fluid flow passing over a heated element;
 (ii) calorimetric sensors that detect the asymmetry of the temperature profile generated by a heated element and caused by the forced convection of the fluid flow; and
 (iii) time of flight (ToF) sensors that measure the time elapsed between the application and the sensing of a heat pulse.

Reviews of thermal fluid flow sensor have been published in (B. Van Oudheusden, "Silicon flow sensors," in Control Theory and Applications, IEE Proceedings D, 1988, pp. 373-380; B. Van Oudheusden, "Silicon thermal flow sensors," Sensors and Actuators A: Physical, vol. 30, pp. 5-26, 1992; N. Nguyen, "Micromachined flow sensors-A review," Flow measurement and Instrumentation, vol. 8, pp. 7-16, 1997; Y.-H. Wang et al., "MEMS-based gas flow sensors," Microfluidics and nanofluidics, vol. 6, pp. 333-346, 2009; J. T. Kuo et al., "Micromachined Thermal Flow Sensors-A Review," Micromachines, vol. 3, pp. 550-573, 2012). Further background can also be found in U.S. Pat. No. 6,460,411 by Kersjes et al.

In A. Van Putten and S. Middelhoek, "Integrated silicon anemometer," Electronics Letters, vol. 10, pp. 425-426, 1974 and A. Van Putten, "An integrated silicon double bridge anemometer," Sensors and Actuators, vol. 4, pp. 387-396, 1983 resistor based anemometers are integrated on chip within Wheatstone bridge configurations. B. Van Oudheusden and J. Huijsing, "Integrated flow friction sensor," Sensors and Actuators, vol. 15, pp. 135-144, 1988 propose a thermal flow sensor, calibrated for friction measurements, wherein thermocouples in addition to heating resistors and an ambient temperature monitoring transistor are integrated on chip. J. H. Huijsing et al., "Monolithic integrated direction-sensitive flow sensor," Electron Devices, IEEE Transactions on, vol. 29, pp. 133-136, 1982, W. S. Kuklinski et al., "Integrated-circuit bipolar transistor array for fluid-velocity measurements," Medical and Biological Engineering and Computing, vol. 19, pp. 662-664, 1981, U.S. Pat. No. 3,992,940 by Platzer and T. Qin-Yi and H. Jin-Biao, "A novel CMOS flow sensor with constant chip temperature (CCT) operation," Sensors and actuators, vol. 12, pp. 9-21, 1987 are examples of transistor based anemometers. One drawback of the previously mentioned citations is that they have a high power dissipation, low sensitivity and slow dynamic response of the sensor.

In D. Moser et al., "Silicon gas flow sensors using industrial CMOS and bipolar IC technology," Sensors and Actuators A: Physical, vol. 27, pp. 577-581, 1991 an array of seven npn transistors are used as heating elements and suspended on a crystal silicon cantilever beam for effective thermal isolation. An ordinary pn diode measures the temperature on the beam. The voltage across nineteen silicon/aluminium thermocouples, with hot junctions on the beam and cold junctions on the substrate, is correlated to the gas flow velocity while the heater is driven at constant power. This device suffers from mechanical fragility and vibration sensitivity.

Similarly, L. Lofdahl et al., "A sensor based on silicon technology for turbulence measurements," Journal of Physics E: Scientific Instruments, vol. 22, p. 391, 1989 present a heating resistor and a heater temperature sensing diode integrated on a cantilever beam. Polyimide is used as thermal isolation material between the beam and the substrate, which affects the mechanical robustness of the beam.

In R. Kersjes et al., "An integrated sensor for invasive blood-velocity measurement," Sensors and Actuators A: Physical, vol. 37, pp. 674-678, 1993 a polysilicon heater, driven at constant heating power, and a first diode, used for heater temperature monitoring, are placed on a silicon membrane. A second diode is placed on the substrate for ambient temperature monitoring. A similar sensor is also presented in A. Van der Wiel et al., "A liquid velocity sensor based on the hot-wire principle," Sensors and Actuators A: Physical, vol. 37, pp. 693-697, 1993, where more transistors, in diode configuration, are connected in series in order to improve the temperature sensitivity of the sensor. The use of silicon as membrane material results in high power dissipation, low sensitivity and slow dynamic response of the sensor.

In U.S. Pat. No. 6,460,411, by Kersjes et al., a silicon membrane perforated by slots of thermally insulating material is proposed but has a more complex fabrication process.

In US20160216144A1 a CMOS flow sensor is disclosed, comprising a heating element and a number of thermocouples. The thermocouples provide an additional thermal dissipation path within the membrane, thus increasing the power dissipation, lowering the sensitivity and slowing down the dynamic response of the sensor.

In E. Yoon and K. D. Wise, "An integrated mass flow sensor with on-chip CMOS interface circuitry," Electron Devices, IEEE Transactions on, vol. 39, pp. 1376-1386, 1992 a multi-measure flow sensor is proposed. However, the manufacturing process is not fully CMOS compatible, and thus more expensive than a fully CMOS process.

N. Sabaté et al., "Multi-range silicon micromachined flow sensor," Sensors and Actuators A: Physical, vol. 110, pp. 282-288, 2004 present a multirange flow sensor using nickel resistors as temperature sensors positioned at different distances from the nickel resistive heater. Nickel is not a standard CMOS material, making the sensor fabrication process more expensive than a fully CMOS process.

In G. De Graaf and R. F. Wolffenbuttel, "Surface-micromachined thermal conductivity detectors for gas sensing." 2012 IEEE International instrumentation and Measurement Technology Conference Proceedings, pp. 1861-1864, a structure comprising a heater for temperature control and two thermopiles for sensing embedded in a dielectric pierced membrane is presented. The membrane is obtained by front-etching through the holes that have no influence on the device working behaviour. This process is not compensated for the effects of flow.

US20180143051A1 presents a structure using four resistors in a full bridge configuration, with at least one external element not affected by the flow to be coupled with any of the previous ones. This design requires a complex circuitry for the read-out, and the use of big resistances to increase the output signal that strongly undermine the insulation provided by the membrane.

Traditional flow sensors based on a hot wire embedded in the membrane are known.

Efforts have also been made to quantify the composition of the fluids by using thermal conductivity sensors.

FIG. 1 shows a cross-section and FIG. 2 shows a top view of a state-of-the-art flow sensor based on a heating and self-sensing element. The device has a substrate 1, which could be based on a semiconductor material such as silicon, a membrane which incorporates one or more dielectric layers 2 and a heater 3. The membrane is defined by back etching (as shown) or front etching using dry or wet etching techniques. When the fluid passes over the top of the membrane 4, the heater 3 cools down due to heat convention losses. This could be simply measured by associating the change in the resistance of the heater with the flow rate, speed, volume or mass flow rates. The heater 3 is connected externally through connections and pads 5 (shown in FIG. 2). Alternatively, the heater could be maintained in a constant temperature or constant resistance mode by modifying the power supplied to the heater element. In this case, one can measure the change in the power due to the flow rate, velocity, volume or mass flow rates.

SUMMARY

Presently available sensors have, among others, the following disadvantages:
- high power dissipation, low sensitivity and slow dynamic response of the sensor;
- mechanical fragility and vibration sensitivity;
- reduced mechanical robustness of sensor supporting structures;
- complex fabrication processes;
- manufacturing processes that are not fully CMOS compatible; and
- manufacturing processes that are expensive.

The devices of the present disclosure are advantageous over the state-of-the-art devices for at least the following reasons:
- thermal isolation of the heated element which reduces power dissipation, increases sensitivity and provides a fast, dynamic response of the sensor;
- reduced mechanical fragility and vibration sensitivity of the membrane structure compared to a beam structure;
- a suitable dielectric material used for the dielectric membrane improves mechanical robustness of the membrane;
- a suitable dielectric material used for the dielectric membrane reduces power dissipation, increases sensitivity and provides a fast, dynamic response of the sensor;
- discontinuities within the membrane mitigate power dissipation, sensitivity and dynamic response issues; and
- the devices are fully CMOS compatible and therefore can be manufactured using fully CMOS compatible processes.

The presently disclosed sensor, termed flow and thermal conductivity sensor is able to measure (i) the convective heat transfer induced by a fluid flow passing over a heated element; and/or (ii) the composition of the fluid based on the different thermal conductivity of each of the components of the fluid flow.

Aspects and preferred features are set out in the accompanying claims.

According to a first aspect of the present disclosure there is provided a flow and thermal conductivity sensor comprising: a semiconductor substrate comprising an etched portion; a dielectric region located on the substrate, wherein the dielectric region comprises at least one dielectric membrane located over the etched portion of the semiconductor substrate; and a heating element located within the dielectric membrane, wherein the dielectric membrane comprises at least one recessed region located between the heating element and an edge of the dielectric membrane.

An edge of the dielectric membrane may refer to a perimeter edge of the dielectric membrane, in other words, the area where the dielectric membrane meets or joins the semiconductor substrate. The area of the dielectric region above the semiconductor substrate may refer to the area of the dielectric region outside the dielectric membrane.

The recessed region may be located between the heating element and the edge of the dielectric membrane spaced from the heating element in the direction of flow. In other words, the recessed region may be spaced from the heating element along an axis defined by the direction of flow through the sensor.

The dielectric region may comprises a dielectric layer or a plurality of layers including at least one dielectric layer. The heating element may be fully embedded or partially embedded within the dielectric membrane. The at least one recessed region may comprise one or more discontinuous regions where the thickness of the dielectric membrane is discontinuous or varies from an average or most common dielectric membrane thickness.

Generally speaking, a dielectric membrane region may be located immediately adjacent to the etched portion of the substrate. The dielectric membrane region corresponds to the area of the dielectric region above the etched cavity portion of the substrate. Each dielectric membrane region may be over a single etched portion of the semiconductor substrate.

The recessed regions or discontinuities in the dielectric membrane provide an interruption (or partial interruption) in the thermal conduction path through the solid of the dielectric membrane. This in turn will mean that the heat path will occur more through the fluid above the recess (via conduction and convention) or through the cavity space formed as a result of the recess (mainly through fluid conduction). In both cases (heat above the cavity space or within the cavity space), the heat dissipation will depend on the thermal conductivity of the fluid.

The recessed regions may be holes (perforations) through the dielectric membrane. This would be advantageous, as the thermal conduction path through the solid of the dielectric membrane will be impeded and this will mean that the thermal conduction will occur through the holes (mainly via conduction) or above the holes (via both conduction and convection), thus facilitating the measurement of the composition of the fluid based on the different thermal conductivity of each of the components of the fluid flow.

The sensor may be a thermal conductivity flow sensor incorporated in a MEMS structure comprising a heating element and at least one other sensing element that is able to detect separately the fluid flow properties, such as velocity, volume flow rate, mass flow rate and the composition the fluid based on the difference in thermal conductivity, specific heat capacity, dynamic viscosity, density (and other thermo-mechanical properties, hereafter simply referred to as thermal properties) of different components of the fluid.

The disclosed sensor could be applicable to a variety of gases and liquids, but we make specific reference to Carbon dioxide ($CO_2$), methane and hydrogen as these specific gases have thermal conductivity properties which are significantly different from those of air. Although we make specific reference to thermal conductivity as the thermo-mechanical property allowing discrimination between fluids, the disclosed devices could utilise any other thermo-mechanical property. The disclosed device could be used, for example, in a breathalyser where flow and CO2 concentration could be measured concomitantly. The disclosed device could also be used in other healthcare, fluidic, consumer, environmental, or smart home applications.

The sensor may comprise a flow and thermal conductivity sensor comprising: a semiconductor substrate, a dielectric membrane, a heating element embedded in the membrane which could act as a sensing element itself, a sensing element or a sensing element pair to sense the flow properties such as fluid flow rate, velocity, flow mass or volume flow rates, at least one hole through the membrane, a further sensing element or a further pair of sensing elements to sense the composition and the concentrations of the components of the fluid based on the difference in thermal conductivities of the components, whereby the at least one recess (could be a hole) is designed and arranged (in terms of area, numbers, if more than one and location) to enhance the sensitivity and selectivity to the concentration of the components of the fluid.

The sensitivity and accuracy to the flow composition (e.g. $CO_2$ percentage or ppm value in air) could be significantly improved by the presence of the holes through the membranes and/or by the flow itself. Higher flow rates or velocities allow for increased signal to differentiate fluids (or components of a fluid) with different thermal conductivities. This is because the thermal losses from the heater through the flow itself are both conductive and convective in nature and the convection (movement of fluid atoms with the flow) helps to enhance heat conduction process through the fluid rather than the solid membrane. As a result, the differential signal due to the presence of a fluid or component of a fluid ($CO_2$) that has a different thermal conductivity than a reference fluid or another component of the fluid (e.g. air) could be enhanced, as more heat conduction occurs through the fluid rather than through the solid dielectric membrane.

The flow sensor may have incorporated within the same device or chip and optionally within the same membrane, a thermal conductivity sensor based on at least one temperature sensing element. The device is able to concomitantly sense properties of the fluid flow such as speed, mass, volume, shear stress as well as the composition of the flow (e.g., whether the fluid, in this case, the gas, has a certain $CO_2$ or hydrogen or methane percentage/ppm within air).

There may be at least one hole through the membrane to connect the upper side of the membrane to the lower side of the membrane via the fluid to be sensed. The at least one hole also disrupts the thermal conduction path through the solid dielectric membrane, forcing more heat to dissipate via convection and conduction through the environment. The presence of the at least one hole also helps to reduce the power consumption of the device (for the same heater temperature), because of the reduction in the heat conduction losses (through the solid membrane). Furthermore, the presence of the at least one hole allows for a lower thermal mass of the membrane thus reducing the time needed for the heater to heat up and cool down.

The at least one hole may be used to enhance the sensitivity/selectivity to any fluid or component of the fluid (e.g. air with a concentration of $CO_2$) with a thermal conductivity that is different to that of a reference fluid or another component of the fluid (e.g. air).

An arrangement and specific design of different holes and different sensing elements is provided to enhance the sensitivity to any fluid or component of the fluid (e.g. air with a concentration of $CO_2$) with a thermal conductivity that is different to that of a reference fluid or another component of the fluid (e.g. air).

There is provided at least one arrangement of different holes and different sensing elements to provide a differential signal between two sensing elements (i.e. pair of sensing elements) that is indicative of the concentration of a particular component of the fluid (e.g. concentration of CO2) in a reference fluid (air). The differential signal provided could be directly proportional with such concentration. The sensing elements may refer to temperature sensing elements and they can be in the form of resistive temperature detectors, diodes, transistors or the thermopile or an array in series or parallel of such elements or a combination of those. The differential signal could be, for example, a voltage difference due to the temperature difference on the pair of the sensing elements.

The arrangement of different holes (or recessed regions) may be placed symmetrically around the heater.

The heater temperature may be modulated by applying different power levels to increase sensitivity and selectivity to different fluid components based on their thermal conductivity variation with temperature.

The heater may be operated in a pulse mode (e.g. driven with a square wave, sinusoidal wave, Pulse Wdth Modulated wave, Pulse Density Modulation, etc.) or continuous mode. The pulse mode has, among others, the advantage of reduced power consumption, reduced electromigration for enhanced device reliability/lifetime and improved fluid properties sensing capabilities.

The at least one recessed region may be arranged to be asymmetrical about an axis defined by the heating element. In use, with no flow or static flow, this allows sensing of different components of a fluid using a differential signal between two sensing elements.

The holes may have an asymmetrical design within the membrane. The arrangement of different holes may be placed asymmetrically within the membrane.

The heating element may be configured to operate as a sensing element, by for example sensing the change in the resistance due to the change in temperature. The heating element may operate simultaneously as both a heating element and a sensing element. The heating element is electrically equivalent to a resistor. The thermal conductivity of most heaters materials (Tungsten, Titanium, Platinum, Aluminium, polysilicon, monocrystalline silicon) varies with temperature. This variation is mostly linear and is characterised by the TCR (Temperature coefficient of resistance). The TCR can be positive or negative, but most metals have a positive and stable TCR, meaning that their resistance increases when the temperature is increased. When current flows through the heating element, the heating element becomes hot, heating the membrane around it. If the heater is operating at the same power, as the fluid flows above the heater, it cools down the heater, due to convection, modifying its resistance (lower resistance for a positive TCR). The heater could also be driven in constant resistance or constant temperature modes and one can associate the change in the power needed to maintain the heater resistance or temperature of the heater the same in the presence of the flow. The sensor may be able to measure the properties of a flow such as flow rate, velocity, mass or volume flow rates as well as the composition of the fluid. The device may be configured to measure flow properties such as flow rate, velocity, mass or volume flow rates by means of sensing the change in the temperature, the change in the voltage, when supplied to a constant current, or the change in the power when the heater is operated in a constant temperature or constant resistance mode.

Alternatively, the flow could be measured by employing sensing elements (such as temperature sensitive elements or temperature sensors) displaced on either side of the heater within the same dielectric membrane and optionally used as a differential pair. The differential pair may be formed of one upstream sensing element and one downstream sensing element. As well as the properties of the flow, the device may be arranged to measure the composition of the flow by having at least one hole or discontinuity in the membrane and by employing at least one other sensing element or a pair of sensing elements (such as temperature sensitive elements or temperature sensors). Optionally, holes or discontinuities may be placed so that they affect less the differential signal between the sensing elements that measure the properties of the flow but they affect significantly more the differential signal between the sensing elements that measure the composition of the flow.

The at least one recessed region may comprises one or more holes. The holes may refer to apertures, perforations or slots extending through an entire height or depth or thickness of the dielectric membrane. This forms a fluid flow path and provides fluid connection between area above and area below membrane.

The at least one of the one or more holes may comprise an elongate slot extending towards opposite edges of the dielectric membrane. The elongate slot may not extend completely to the edges of the dielectric membrane or completely isolate the dielectric membrane either side of the elongate slot. The elongate slot increases thermal isolation across a width of the dielectric membrane of the device. Optionally the elongate slot may be extending in a same direction as one or more heating elements and/or sensing elements. The elongate slots may be, for example, rectangular, square, or semicircle.

The one or more holes may comprise an array of perforations. The perforations may comprise individual holes significantly smaller than a width of the dielectric membrane of the device. The array of perforations may can extend substantially across a width of the device.

The at least one recessed region may comprise a partial recess within the dielectric membrane. The partial recess or trench may extend from a top surface of the dielectric membrane or may extend from a bottom surface of the dielectric membrane. The partial recess may extend partially through a height or depth or thickness of the dielectric membrane. The at least one perforation may be in the form of a trench formed from the top or the bottom surface but not penetrating the other surface.

The discontinuities may be referred to as a gap in the membrane from the top surface to the bottom surface. Though, not as effective in terms of the thermal performance, a discontinuity could also refer to a trench or partial hole created from either the top or the bottom surface (if an upside-down membrane is used) without penetrating the other surface. The advantage of such partial holes is that they could impact less the mechanical strength of the membrane and in some cases they may be easier to be manufactured. Moreover, such partial holes could be used to hermetically seal the bottom side of the membrane or allow no fluid penetration below the membrane.

The at least one recessed region may have a meander shape. In other words, the discontinuity may have a non-standard shape such as a concertina or corrugated shape formed of a series of regular sinuous curves, bends, or meanders.

The sensor may further comprise one or more further sensing elements. There may be one further sensor element or there could be more than one further sensing element.

The one or more further sensing elements may measure a parameter in conjunction with heating element operating as a sensing element.

The one or more further sensing elements may comprise at least a pair of sensing elements located on opposing sides of the heating element. The at least a pair of sensing elements may comprise an odd number of sensing elements or may comprise a plurality of pairs of sensing elements. One or more further sensing elements may be laterally spaced from the heating element and located on a first side of the heating element and one or more further sensing elements may be laterally spaced from the heating element and located on a second side of the heating element, wherein the first side and the second side are opposite sides of the heating element.

The at least one recessed region may be located between a first further sensing element of the at least a pair of sensing elements and the heating element and at least one other recessed region may be located between a second further sensing element of the at least a pair of sensing elements and an edge of membrane. This thermally isolates the first further sensing element from the heating element and thermally isolates the second further sensing element from the semiconductor substrate around the edge of the membrane. Therefore, the thermal differential between the first further sensing element and the second further sensing element is more sensitive to a change in gas concentration and composition. This asymmetric arrangement of discontinuities can sense different components of a fluid using a differential signal between the two sensing elements, even when used with no flow or static flow.

One of the first or second further sensing elements may be located upstream of the flow from the heating element and the other of the first or second further sensing elements may be located downstream of the flow from the heating element. This allows properties, variables, or parameters of a flow to be measured.

The at least one discontinuity may be placed laterally within the membrane between the heater and the sensing element on one side of the heater (e.g. a hot wire placed in the middle of the membrane), and another at least one discontinuity could be placed laterally within the membrane between the sensing element and the edge of the membrane on the other side of the heater. Possibly the two discontinuities or set of discontinuities may have similar surface area. Optionally the two sensing elements may be identical in terms of dimensions and lateral distance from the heater and could be done in the same fabrication process, for example during CMOS steps prior to membrane etching.

The sensor may comprise at least two thermopiles, at least one upstream and at least one downstream with reference to the direction of the flow, at least one hole laterally placed between one of the thermopiles and the heater.

At least one hole or discontinuity may be placed laterally within the said dielectric membrane between the heater and one sensing element. At least one other hole or discontinuity may be placed laterally within the said dielectric membrane between one other temperature sensing element and the edge of the said membrane.

The sensor may sense a static flow or a no flow condition (zero flow rate) based on the variation of the heater resistance with the temperature or based on a pair of matched sensing elements placed laterally at the same distance from the heater or based on symmetrical thermopile placed around/across the heater. At least one other sensing element or an additional pair of sensing elements or an additional heater/sensing element may be used to measure the concentrations of different components of the fluid based on their different thermal conductivities.

The flow/thermal conductivity sensor may also measure "a no flow condition" i.e. zero flow condition, static flow, or negligible flow. This could be done by measuring the signal between two matched sensing elements placed symmetrically either side of the heater. Alternatively, the zero flow condition can be identified by measuring the change in the resistance of the heater or the change in the power applied to the heater to maintain a constant resistance/power against previously calibrated values (base line values). The sensitivity and selectivity to the flow composition is enhanced by using extra sensing elements and symmetrical or asymmetrical holes and/or an additional heater as described in the previous embodiments.

The at least one recessed region may be located between the heating element and at least one of the one or more further sensing elements. For example, this may include a wire extending across the membrane and/or thermopiles on the dielectric membrane, with cold junctions on the membrane.

At least one of the one or more further sensing elements may be configured to measure a differential value across the heating element. For example, they may be used to measure a change in temperature across the heating element. At least one thermopile may be placed symmetrically around/across the heater, and the voltage difference between the thermopile terminals may be indicative of the flow properties, while the sign of the voltage may be indicative of the direction of the flow.

At least one of the one or more further sensing elements may be configured to measure a differential value between the dielectric membrane and the dielectric region above the semiconductor substrate. For example, a thermopile may be arranged to have its hot junction located on the dielectric membrane and its cold junction located on the dielectric region above the semiconductor substrate i.e. outside the dielectric membrane region.

Two thermopiles may be arranged on either side of the heating element, both with their hot junctions located on the dielectric membrane and their cold junctions located outside the dielectric membrane region. As both sets of cold junctions outside the dielectric membrane would be at substantially the same temperature, the difference between the two hot junctions could be used to measure a change in temperature across the heating element. The cold junctions of the at least two thermopiles may be placed outside the membrane and connected together physically or electrically.

The at least one recessed region may be located between at least one of the one or more further sensing elements and an edge of the dielectric membrane. This decreases thermal conduction through the dielectric membrane, between the sensing element and the edge of the dielectric membrane. The temperature of the sensing element is therefore more dependent upon the concentration and composition of any fluid present in the at least one discontinuity between the sensing element and the edge of the dielectric membrane.

The one or more further sensing elements may comprise resistive temperature detectors, diodes, or thermopiles. Thermopiles may be used measure a temperature difference between the dielectric membrane and the dielectric region above the substrate, or may be used to measure a temperature difference across the heating element. Compared to the thermopiles, diodes and detectors have reduced thermal losses to the semiconductor substrate as they are located completely on or within the dielectric membrane. One type of sensing element may be used or a combination of different types of sensing elements may be used.

The sensing elements may be temperature sensitive and may be any of resistive temperature detectors, bolometers, diodes, transistors or thermopiles, or an array in series or parallel or a combination of those.

The sensing elements can also be made of thermopiles. A thermopile comprises one or more thermocouples connected in series. Each thermocouple may comprise two dissimilar materials which form a junction at a first region of the membrane, while the other ends of the materials form a junction at a second region of the membrane or in the heat sink region (substrate outside the membrane area), where they are connected electrically to the adjacent thermocouple or to pads for external readout. The thermocouple materials may comprise a metal such as aluminium, tungsten, titanium or combination of those or any other metal available in the process. Alternatively the thermocouple materials may comprise thermocouples based on n-type and p-type silicon or polysilicon or combinations of metals and semiconductors. The position of each junction of a thermocouple and the number and the shape of the thermocouples may be any required to adequately map the temperature profile distribution over the membrane to achieve a specific performance.

The choice of the shape, position and number of temperature sensing elements, the heating elements and the number of holes or the area of holes within the membrane may generate the temperature profile and/or map the temperature profile distribution over the membrane to achieve a specific performance, and can result in multi-directional, multi-range, multi-properties sensing capabilities. For instance, the flow sensor may be designed to sense both flow rate and flow direction, or flow rate, flow direction and fluid composition based on thermal conductivity, or any other combination of fluid properties. The sensing elements formed within the dielectric membrane, may be configured as a temperature resistor detector (TRD) or a bolometer, a diode, a transistor or an array of transistors or diodes for enhanced sensitivity and selectivity.

The sensing elements could be used in a differential way to sense (i) the flow properties, such as velocity, flow rate, volume or mass flow rates of the flow (by measuring the signal difference between the upstream and the downstream sensing elements) or (ii) the flow composition based on the difference in the thermal conductivity between different components of the fluid (e.g. hydrogen has a much higher thermal conductivity than air; $CO_2$ has a lower thermal conductivity than air).

Holes within the membrane may be placed at a specific location and may be used to enhance the differential signal between the sensing elements to detect with higher accuracy the composition of the fluid. Additionally, the heater temperature may be modulated by electric pulses and to different levels to increase selectivity and detect the concomitant presence of more than one fluid component with different thermal conductivities. For example, hydrogen and CO2 percentage/ppm concentration in air flowing at the surface of the sensor can be detected concomitantly by modulating the temperature of the heater and based on the fact that the thermal conductivity of these gases (CO2 and air) change differently with the increase in temperature.

The heater or heating element may also be used as a temperature sensing device. The heat exchange between the heater and the fluid can then be measured through the change in the resistance of the heater itself, and correlated to the at least one property of the fluid (e.g. velocity, flow rate, flow mass or volume flow rates, exerted wall shear stress, pressure, temperature, direction).

Additional sensing elements and holes or discontinuities through the membrane may be placed at specific locations to enable fluid discrimination (or differentiation). For instance, the flow sensor can sense if the fluid is in gas form or liquid form, or the sensor can discriminate between different fluids (e.g. between air and $CO_2$), or if the fluid is a mixture, the sensor can measure the mixture ratio, by modulating the temperature level of the heater or by operating the heater in a pulse mode and measuring the time of flight to a sensing element placed at a specific location. Both qualitative (e.g. liquid or gas form) and quantitative information (e.g. gas concentration) of the fluid properties can be obtained.

The sensor may be configured to operate as a flow sensor. The sensor may be configured to measure or sense a property of a fluid flow. Alternatively, the sensor may be configured to measure properties of a fluid when there is no flow of fluid or a static flow.

The sensor may comprise a first pair of further sensing elements and a second pair of further sensing elements, wherein a differential signal between the first pair of further sensing elements may be configured to measure a flow property and wherein a differential signal between the second pair of sensing elements may be configured to measure a property of a composition of the flow.

The sensor may include two pairs of sensing elements wherein the differential signal between one pair of sensing elements is used to extract flow properties such as flow rate, flow direction, velocity or flow mass or flow volume rates and the differential signal between the other pair of sensing elements is used to detect different components of the fluid and their concentrations based on their different thermal conductivities.

Different components of the fluids may be sensed based on their different thermal conductivities by using a differential signal between two sensing elements.

In use, the heating element may extend in a direction perpendicular to the direction of flow through the sensor. The heating element may not be at an exact right angle to the direction of flow, and may extend in a diagonal direction or at an acute angle to the direction of flow however one component of the extension of the heating element may be perpendicular to the flow. Optionally, the heating element may be substantially perpendicular or may be arranged at an angle within 10° to the direction perpendicular to the flow through the sensor.

The sensor may comprise a further heating element, and wherein, in use, the further heating element may extend in a direction parallel to the direction of flow through the sensor. The heating element may not be exactly parallel to the direction of flow, and may extend in a diagonal direction or at an acute angle to the direction of flow however, one component of the extension of the heating element may be parallel to the flow. The further heating element may be perpendicular to the heating element, or may be located at an acute angle to the heating element. Optionally, the heating element may be substantially parallel or may be arranged at an angle within 10° to the direction of flow through the sensor.

An additional or further heater or heating element may be incorporated within the same dielectric membrane, where the two heaters may be operated at different times in pulse conditions and where the additional heater is used to enable the detection of the different components of the fluid and their concentrations based on their different thermal conductivities.

The sensor may further comprise one or more further sensing elements configured to measure a differential signal across the further heating element. The further sensing elements may be at least a pair of further sensing elements located laterally spaced from each other on either side of the further heating element. The further sensing elements may be aligned with and/or extend in a direction parallel to the direction of fluid flow through the device. The further sensing elements element may not be exactly parallel to the direction of flow, and may extend in a diagonal direction or at an acute angle to the direction of flow however, one component of the extension of the further sensing elements may be parallel to the flow. The temperature difference between the laterally spaced further sensing elements about the further heating element may be less dependent on flow rate and properties and more dependent on gas concentration and composition.

The first heater may be in the form of a hotwire and may be orthogonal to the direction of the flow and the additional heater may be in the form of a hotwire and may be aligned to the direction of the flow.

There may be at least one additional heater (hotwire or hot plate) provided that can be operated to discriminate between the presence and the parameters of the flow and the composition of the fluid that flows. The heaters could be operated in pulse mode at different times. One heater could be operated to sense the flow properties, such as flow rate, velocity, mass or volume flow rate, by measuring its resistance in the presence of flow or by monitoring the temperature/power of a sensing element or the differential signal of a pair of sensing elements and the second heater could be used to enable the detection of the composition of the fluid.

Optionally the first heater which contains a hot wire and/or sensing elements has a direction that is orthogonal to the direction of the flow to enhance the sensitivity to flow rate/velocity, while the second heater is aligned to the flow direction to be less affected by the flow rate/velocity and instead measure the composition of the fluid.

The two heaters may be made of different metal layers (e.g. Al, Tungsten, Copper, Titanium, Platinum etc.) available in the fabrication process (e.g. CMOS process).

Around the second heater a pair of sensing elements and holes or discontinuities may be provided to enhance the detection of the fluid components. At least one hole could be placed laterally within the membrane between the second heater and the sensing element on one side of the second heater and another at least one hole could be placed laterally within the membrane between the sensing element and the edge of the membrane on the other side of the second heater. The two holes or set of holes may have similar surface area. The two sensing elements may be identical in terms of dimensions and lateral distance from the heater and may be manufactured in the same fabrication process, for example during CMOS steps prior to membrane etching.

The first heater may be a hot wire made in a first metal of the CMOS process (metal 1) and the second heater may be a hot wire placed within the membrane orthogonally to the first heater and could be made of a different metal layer (e.g. metal 2) so that the two heaters do not have an electrical connection (short).

The sensing element or sensing elements may be one or more thermopiles. Alternatively at least one sensing element in the form of a thermopile may be placed symmetrically around or across both the heaters. The hot junction of the at least one sensing element can be placed on one side of the first heater and the cold junction on the other side of the first heater, both within the membrane at a certain distance from the heater and the edge of the membrane. The heaters could be operated in pulse mode at different times. The first heater, perpendicular to the direction of the flow could be operated to sense the flow properties, such as flow rate, velocity, mass or volume flow rate, by measuring the voltage drop of the thermopile, while the second heater, aligned to the flow could be operated to sense the flow composition by measuring the voltage drop of the thermopile. Both the first and/or the second heaters could be modulated in temperature to increase the accuracy of the measurements and improve sensitivity/selectivity to different components of the flow. Holes could be provided to reduce the thermal losses and enhance sensitivity/selectivity to different components of the flow. Optionally, holes could be placed asymmetrically to provide a larger differential signal on the thermopile and thus provide a further enhancement in the sensitivity/selectivity to different components of the flow.

The temperature of the heater may be modulated and the voltage difference between the thermopile terminals at different temperatures may be assessed against reference values and the difference between the two is indicative of the flow composition.

Alternatively at least one sensing element in the form of a thermopile may be placed symmetrically around or across the heater. The hot junction of the at least one sensing element can be one side of the heater and the cold junction on the other side of the heater, both within the membrane at a certain distance from the edge of the membrane. Holes could be placed asymmetrically or symmetrically within the membrane in the space between the at least one thermopile and the edge of the membrane. The difference in voltage (proportional with the different in temperature) between the hot junction and cold junction is indicative of the flow properties. The heater could be modulated in temperature and the thermopile voltage (the voltage drop between the hot junction and cold junction) could be assessed against a calibrated data to indicate the composition of the flow. This could be also correlated to a measurement of the resistance of the heater. Alternatively other sensing elements such as additional resistive temperature detectors or other thermopiles could be provided to enhance sensitivity/selectivity to different components of the flow. The holes could be placed laterally and asymmetrically around these additional sensing elements to provide further enhancement in the sensitivity/selectivity to different components of the flow.

The temperature sensing elements may be formed as long elements which may be aligned to either the first or the additional/second heater depending if their primary purpose is to sense properties of the flow such as flow rate or speed or if their primary purpose is to sense the composition of the fluid and the concentrations of different components of the fluid respectively.

The dielectric membrane may be circular and the at least one recessed region may have an arc shape. The heating element and sensing elements may also have arc shapes. The centre of a circle that the arcs lie on may correspond to a centre of the circular membrane. This improves use of the membrane area and increases thermal performance.

The sensor may further comprise a flow mechanism configured to provide or control a flow through the sensor. For example, if a flow with a known velocity is provided, then the sensor may be used to measure another variable more accurately or precisely, such as fluid composition or concentration. The sensor may be measuring the flow of known velocity but using this information to determine other properties and therefore may not be operating purely or strictly as a flow sensor.

The flow mechanism may comprise at least one additional heater configured to produce a temperature gradient across the sensor. The heaters may be located external to the sensor within manifolds or could be one or more heaters located on the same dielectric membrane or a different membrane but monolithically integrated with the sensor.

The sensor may comprise a flow making device or flow mechanism such as a micro-fan, micro-pump or micro-valve to create and/or manipulate a flow at the surface of the sensor as to enable more accurate measurement of the concentrations of different components of the fluid based on their different thermal conductivities. The flow mechanism may be able to create or manipulate flow (e.g. micro-pump or an additional heater that creates a temperature gradient and flow via thermophoresis or thermodiffusion that is adjacent to the flow/thermal conductivity sensor).

The flow mechanism or flow making device could serve to enhance the signal/accuracy of the composition of the fluid present. For example in a normally static flow, the $CO_2$ detection in low values of ppm (say 500 ppm with a precision of 100 ppm) is difficult as the signal provided by the thermal conductivity sensor could hidden within the noise levels. To enhance/amplify the signal, the flow could be generated by the device for a period of time that allows easier or higher accuracy detection, by enhancing the differential signal between two sensing elements. The flow sensor could be used to calibrate or measure the flow created on the surface of the sensor.

The flow itself could be used to enhance the signal/accuracy detection of the fluid. A micropump to create fluid flow or at least one additional heater embedded in the same membrane or on a different membrane within the same substrate or placed externally could be used to create a gradient of temperature as to create a flow, or to enhance the detection of the flow components by using their different thermal properties (thermal conductivity, thermal convection, thermal times). Such device could also be integrated with an ASIC and/or placed within a manifold.

An additional heater may be provided within the same system or the same package or the same device or the same membrane to create a temperature gradient and via thermodiffusion a flow at the surface of the sensor as to enable more accurate measurement of the concentrations of different components of the fluid based on their different thermal conductivities.

The flow mechanism or flow making device could serve to enhance the signal/accuracy of other gas sensors such as those based on metal oxide, electrochemical or catalytic. Taking the example of a gas sensor, the flow could help to enhance the binding or diffusion of gas molecules into the metal oxide and thus increase the sensitivity or the detected signal for that gas. An example could be a volatile organic compound or nitrogen dioxide or carbon monoxide sensor. The flow making device could enhance the reaction of the gas to the metal oxide layer deposited onto dedicated electrodes placed on a membrane above the heater or in the proximity of a heater. A flow sensor, adjacent or monolithically integrated with the gas sensor could serve to measure accurately the flow. An array of gas sensors could be provided to enhance the selectivity while different flow rates could be used to optimise the sensitivity for each gas. The flow making device could be the same as described above (e.g. micropump, microfan, or based on additional heaters).

Alternatively the flow sensor could be integrated on the same membrane with the gas sensor to save space and decrease the cost. In such case the flow sensor and the gas sensor may be operated in pulse conditions. In one pulse the flow sensor is active and able to measure the flow rate and fluid properties while in another pulse the gas type and concentration could be detected and measured.

Alternatively the flow sensor could also comprise a thermal conductivity sensor and integrated in the same system/package or chip with at least one metal oxide, catalytic or electro-chemical gas sensor. The flow sensor would be able to measure the flow rate, the thermal conductivity sensor would be able to measure gases such as CO2 or Hydrogen based on the thermal conductivity difference between such gases and air, and the gas sensor could measure other gases such as NO2, CO or volatile organic compounds. The gas sensor could also measure hydrogen and in this way help the thermal conductivity sensor to differentiate between CO2 and hydrogen presence.

The sensor may further comprise an application specific integrated circuit (ASIC) coupled to the sensor. The ASIC may be located underneath the sensor, for example using a die stack technique. Alternatively, the ASIC may be located elsewhere. The ASIC may be connected to the sensor using wire bonding and pads, or using through-silicon-vias (TSV) extending through the semiconductor substrate.

An ASIC may be provided within the same system or the same package or on-chip to provide electronic circuitry to drive, read-out signals and process signals from the sensor. The ASIC may be placed in a stack die configuration under the sensor and the sensor and ASIC are placed within a manifold.

Analogue/digital circuitry may be integrated on-chip. Circuitry may comprise IPTAT, VPTAT, amplifiers, analogue to digital converters, memories, RF communication circuits, timing blocks, filters or any other mean to drive the heating element, read out from the temperature sensing elements or electronically manipulate the sensor signals. For example, it is demonstrated that a heating element driven in constant temperature mode results in enhanced performance and having on-chip means to implement this driving method would result in a significant advancement of the state-of-the-art flow sensors. The driving method known a $3\omega$ may be implemented via on-chip means, or any other driving method, such as constant temperature difference and time of flight, needed to achieve specific performance (e.g. power dissipation, sensitivity, dynamic response, range, fluid property detection, etc.). In absence of on-chip circuitry, this disclosure also covers the off-chip implementation of such circuital blocks when applied to a flow sensor having one or more features described in any of the previous embodiments. Such off-chip implementation may be done in an ASIC or by discrete components, or a mix of the two.

The device may be packaged in a metal TO type package, in a ceramic, metal or plastic SMD (surface mount device) package. The device may also be packaged directly on a PCB, or with a flip-chip method. The device may also be embedded in a substrate, such as a customised version of one of the previously mentioned package, a rigid PCB, a semi-rigid PCB, flexible PCB, or any other substrate, in order to have the device surface flush with the substrate surface. The package can also be a chip or wafer level package, formed for example by wafer-bonding.

The device may also be assembled within a manifold which provides an inlet, outlet and a pre-defined channel through which the fluid flow takes place. The manifold provides protection to the device as well as allowing easier and more controllable measurement of the flow or the fluid composition. The ASIC or external read-out circuitry may also be placed in the same manifold in a lateral or die stack configuration.

The flow sensor may have through silicon vias (TSV), to avoid the presence of bond wires in proximity of the sensitive area of the device which might affect the flow sensor readings. Advantageously, a flow sensor with TSV can enable 3D stacking techniques. For instance the flow sensor chip can sit on top of an ASIC, thus reducing the sensor system size.

The semiconductor substrate may be silicon and the dielectric membrane may be formed mainly of oxide and nitride materials and where the heater is made of a metal such as tungsten, titanium, copper, aluminium, gold, platinum or a combination of those or a semiconductor such as highly doped n type or p type silicon or polysilicon and where the heater has a shape of a meander, spiral or a hotwire.

The starting substrate may be any semiconductor such as silicon, silicon on insulator (SOI), Silicon Carbide, Sapphire or Diamond. In particular the use of silicon is advantageous, as it guarantees sensor manufacturability in high volume, low cost and high reproducibility. The use of a silicon substrate could also enable on-chip circuitry for sensor performance enhancement and system integration facilitation. Such on-chip circuitry could be implemented by using analogue or digital or mixed-signal blocks placed outside the dielectric membrane.

The dielectric membrane or multiple membranes may be formed by back-etching using Deep Reactive Ion Etching (DRIE) of the substrate, which results in vertical sidewalls and thus enabling a reduction in sensor size and costs. However, the back-etching can also be done by using anisotropic etching such as KOH (Potassium Hydroxide) or TMAH (TetraMethyl Ammonium Hydroxide) which results in slopping sidewalls. The dielectric layers within the membrane which could be formed by oxidation or oxide deposition could be used as an etch stop during the DRIE or wet etching processes. The membrane can also be formed by a front-side etch or a combination of a front-side and back-side etch to result in a suspended membrane structure, supported only by two or more beams.

The membrane may be circular, rectangular, or rectangular shaped with rounded corners to reduce the stresses in the corners, but other shapes are possible as well. Additionally holes may be formed within the membrane to reduce the thermal dissipation via the heat conduction through the dielectric membrane and enhance the heat loss via heat convention and conduction in the regions below and above the membrane, and optionally in the path of the fluid (above the membrane). Optionally the holes or discontinuities may be made by front etching after the membrane is formed.

The dielectric membrane may comprise silicon dioxide and/or silicon nitride. The membrane may also comprise one or more layers of spin on glass, and a passivation layer over the one or more dielectric layers. The employment of materials with low thermal conductivity (e.g. dielectrics)

enables a significant reduction in power dissipation as well as an increase in the temperature gradients within the membrane with direct benefits in terms of sensor performance (e.g. sensitivity, frequency response, range, etc.). Temperature sensing elements or heaters made of materials such as monocrystalline or polycrystalline semiconductors or metals could be suspended or embedded in the dielectric membrane.

The membrane may also have other structures made of metal or other conductive or other materials with higher mechanical strength. These structures can be embedded within the membrane, or may be above or below the membrane, to engineer the thermo-mechanical properties (e.g. stiffness, temperature profile distribution, etc.) of the membrane and/or the fluid dynamic interaction between the fluid and the membrane. More generally these structures can be also outside the membrane and/or bridging between inside and outside the membrane.

The fluid sensed may be a gas, and the gas may be made of air and the components of interest could be any of $CO_2$, methane or hydrogen or other gases that have different thermal conductivity than that of air.

The substrate may comprise: more than one etched portion; a dielectric region located on the substrate, wherein the dielectric region comprises a dielectric membrane over each area of the etched portion of the substrate. At least one membrane may contain any combination of the features described above. A second membrane may employ more holes or discontinuities, a larger area of holes or discontinuities, or holes or discontinuities at a different location. A differential signal can be measured between a sensing element on the first membrane and a sensing element placed on the second membrane to detect the composition of the fluid in addition to the flow properties of the fluid.

The flow/thermal conductivity sensor can also be operated in a static flow (zero speed/flow rate) and be used to detect the presence of a particular component of the fluid. The flow sensor elements can detect the absence of the flow while the at least one additional sensing element (or a pair of sensing elements operated differentially) could detect the flow components (for example the $CO_2$ ppm in air).

The flow/thermal conductivity sensor may be used in applications ranging from consumables (such as personal care products or white goods), smart energy (e.g. HVAC, gas metering) and industrial automation (e.g. leakage testing, dispensing, analytic instruments) to medical (e.g. breathalyser, spirometry, capnometry, respirators, inhalers, drug delivery) and fluid dynamics research (e.g. turbulence measurements, flow attachment). Interestingly, this sensor also enables application in harsh environments (ambient temperature from cryogenic regime up to 300° C.), such as boilers, automotive, space and others.

According to a further aspect of the present disclosure, there is provided a flow sensing device comprising: a flow sensor housing; and a sensor as described above, located within the flow sensor housing. The flow sensor housing may comprise an inlet and an outlet and a fluid flow path for directing a fluid flow through the sensor. The sensor may be packaged within a packaging house or manifold with an inlet, outlet and a channel to provide more accurate measurements of the flow.

According to a further aspect of the present disclosure there is provided a method of manufacturing a sensor, the method comprising: forming at least one dielectric membrane on a semiconductor substrate comprising an etched portion, wherein the dielectric membrane is over an area of the etched portion of the semiconductor substrate; forming a heating element within the dielectric membrane; and forming at least one recessed region within the dielectric membrane and located between the heating element and an edge of the dielectric membrane.

The method of manufacturing may comprise: forming at least one dielectric membrane on a substrate comprising an etched portion, wherein the dielectric membrane is over an area of the etched portion of the substrate; forming at least one hole through the dielectric membrane, forming a heater and one or more sensing elements to sense the flow properties such as velocity, flow rate, volume and mass flow rates and the composition of the fluid that flows based on different thermal properties of the fluid components.

BRIEF DESCRIPTION OF THE FIGURES

Some embodiments of the disclosure will now be described by way of example only and with reference to the accompanying drawings, in which.

DETAILED DESCRIPTION OF THE PREFERRED EMBODIMENTS

Figure 1:
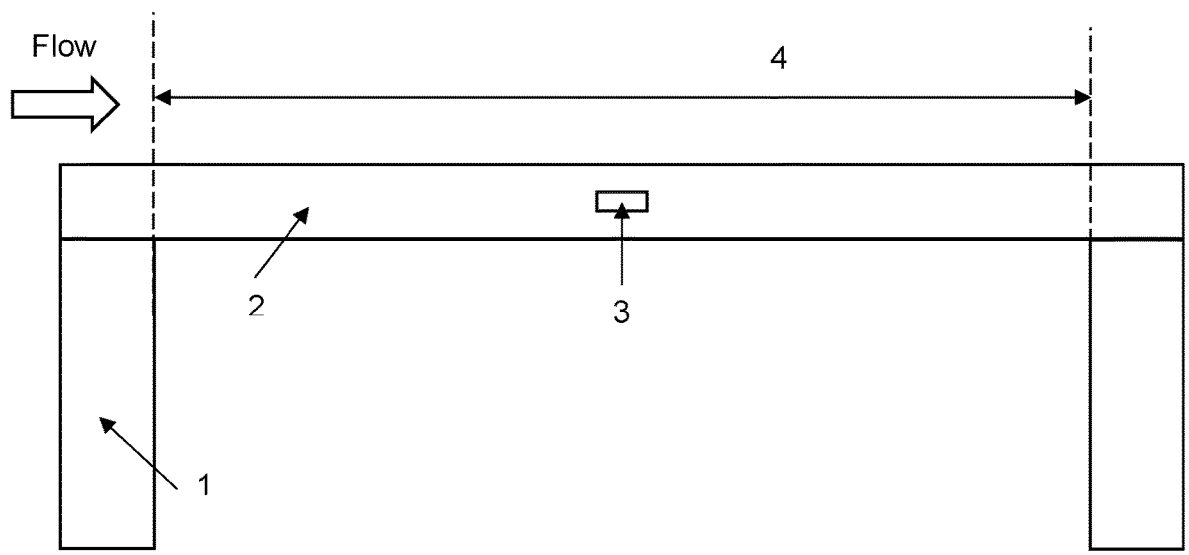
FIG. 1 shows a cross-section of a state-of-the-art flow sensor based on a heating and self-sensing element.
Figure 2:
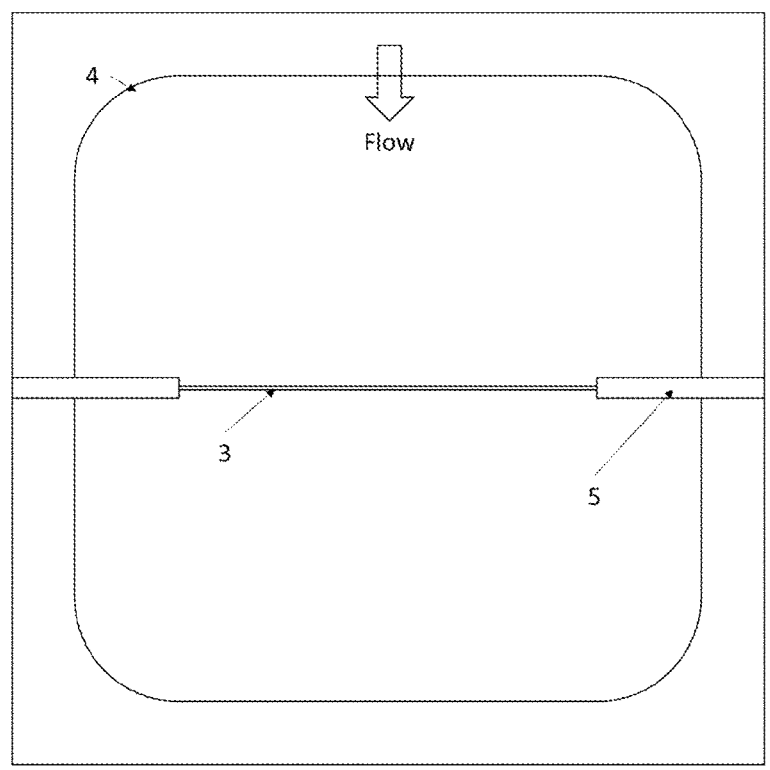
FIG. 2 shows a top view of a state-of-the-art flow sensor based on a heating and self-sensing element.

Some examples of the disclosed device are given in the accompanying figures.

LIST OF REFERENCE NUMERALS

Figure 3:
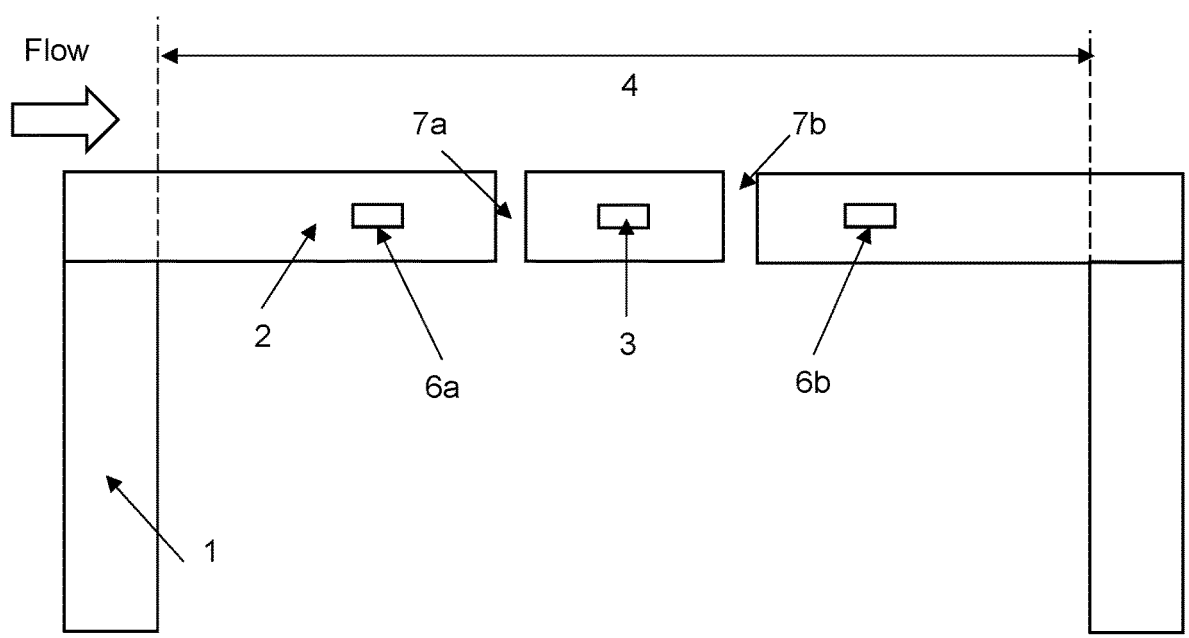
FIG. 3 illustrates schematically a cross-section of a sensor according to an embodiment of the disclosure.
Figure 4:
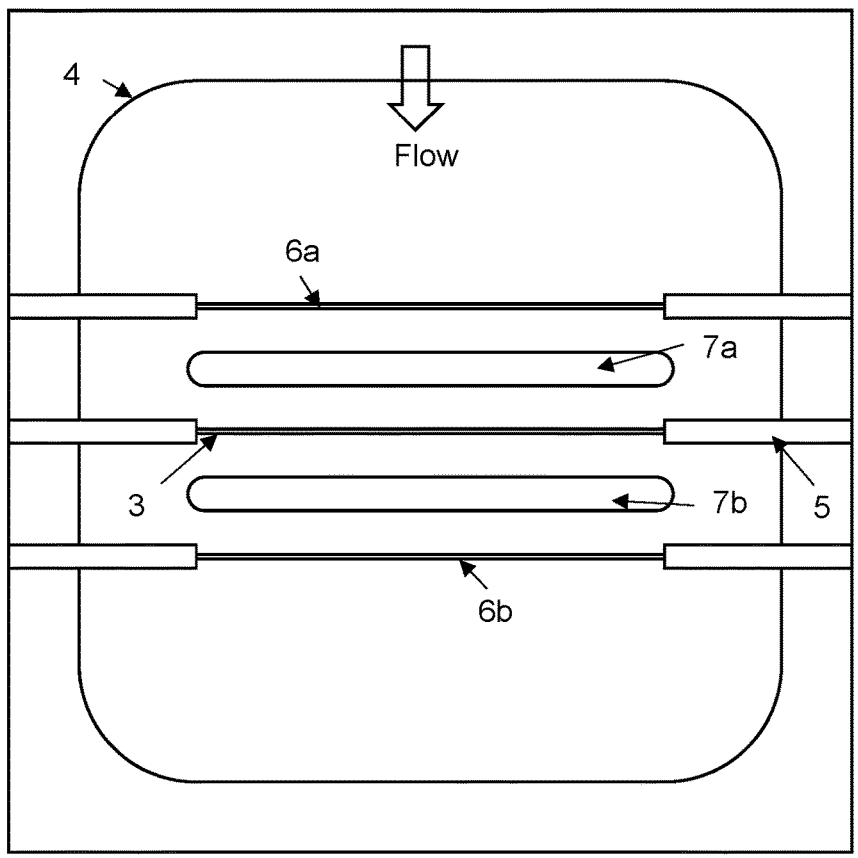
FIG. 4 illustrates schematically a top-view of the sensor of FIG. 3 according to an embodiment of the disclosure.

1. Semiconductor substrate (e.g. silicon)
2. Dielectric membrane (e.g. oxides and nitrides)
3. First heater or heating element—Hot wire (e.g. tungsten, platinum, titanium)
4. Etched area defining the membrane
5. Biasing tracks
6. Sensing elements
   a. Upstream
   b. Downstream
   c. Upstream far
   d. Downstream far
7. Membrane holes or recesses
   a. Upstream
   b. Downstream
   c. Upstream far
   d. Downstream far
   e. Upstream adjacent to heater
   f. Downstream adjacent to heater
8. Second heater or heating element
9. Thermopiles
   a. Up left
   b. Down left
   c. Up right
   d. Down right
10. Hotplate
11. Additional heater on a separate microhotplate
12. Membrane of separate microhotplate
13. ASIC (or read-out, transducing and drive circuit)
14. Bond Wire
15. and 16. Bond Pads
17. Package Base
18. Package Sidewalls
19. Package Lid
20. Flow Mechanism
21. and 22. Flow Heaters
91. Hot Junction of a Central Thermopile
92. Cold Junction of a Central Thermopile FIG. 3 illustrates schematically a cross-section of a sensor according to an embodiment of the disclosure and FIG. 4 illustrates schematically a top-view of the sensor of FIG. 3.

The device has a semiconductor substrate 1, a dielectric layer or dielectric region 2 suspended on or over an etched area defining the dielectric membrane 4, and a heater or heating element 3. The heating element extends in a direction substantially perpendicular to the direction of flow through the sensor. When the fluid passes over the top of the membrane 4, the heater 3 cools down due to heat convention losses.

In this embodiment, there are two temperature sensing elements 6a (upstream) and 6b (downstream), placed symmetrically on opposing sides of the heater. The two temperature sensing elements may be considered further sensing elements as the heating element itself can act a sensing element. The two sensing elements could be made of the same material as the heater (e.g. Tungsten, polysilicon, platinum, Aluminium) or could be a different material with a stable and relatively high temperature coefficient of resistance (TCR). Alternatively, diodes or thermopiles could be used for the sensing elements. The two sensing elements may measure a differential across the heating element.

Discontinuities or recessed regions (in this embodiment holes) 7a and 7b through the membranes (processed optionally by front etching) are placed in a symmetrical way. The holes minimise the thermal path through the solid dielectric membrane, forcing more heat to dissipate via convection and conduction through the environment (mostly above the membrane via conduction and convection), but partly also via heat conduction through the space formed by the holes or below the membrane (in case of holes). The presence of the holes also helps to reduce the power consumption of the device (for the same heater temperature), because of the reduction in the total heat losses. Furthermore, the holes help to reduce the thermal response time (increase the speed at which the heater heats up when supplied with an electrical power pulse) due to the decrease in the thermal mass of the membrane. In this embodiment, the holes are elongate slot extending towards opposite edges of the dielectric membrane.

The change in the resistance of the heater 3 is associated with the flow rate, speed, volume or mass flow rates. Alternatively, the heater 3 could be maintained in a constant temperature or constant resistance mode by modifying the power supplied to the heater element. In this case, one can measure the change in the power due to the flow rate, velocity, volume or mass flow rates. In the presence of the flow, 6b (the downstream sensing element) sees a higher temperature than 6a (the upstream sensing element). The temperature difference between 6b and 6a increases with the flow rate (or flow velocity). In the example of sensing the CO2 concentration in air, given the fact that CO2 has a lower thermal conductivity than air, less heat will dissipate through the environment making the increase in the temperature between 6b and 6a less for a given flow rate. One can associate the change in the differential temperature between the two temperature sensing elements 6b and 6a with the CO2 concentration in air for a given flow rate (which can be measured by the heater itself 3).

The opposite effect occurs if a certain concentration of hydrogen is present in the air. Hydrogen has a higher thermal conductivity than air and therefore the increase in the temperature between 6b and 6a will be higher for a given flow rate.

The temperature difference could be translated into a voltage difference or resistance difference, depending on the temperature sensing element employed. For diodes supplied with constant current, or for thermopiles, the voltage difference is appropriate. For Resistive Temperature Detectors (RTD), several read-out techniques could be employed such as using instrumentation bridges to measure change in the resistance or using current mirrors and sensing the voltage difference.

However, the sensitivity of this arrangement may be limited as the change in the temperature of the two sensing elements due to the fluid composition (e.g. $CO_2$ in air) is relatively low compared to the change in the temperature due to the flow rate via convection.

Figure 5:
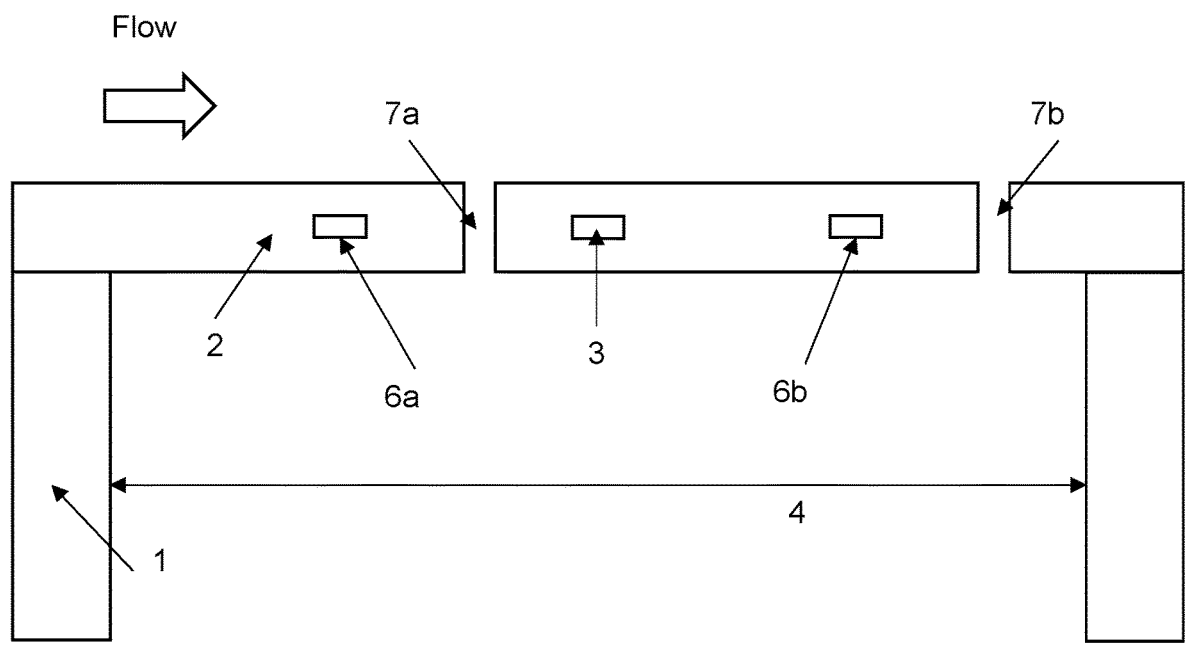
FIG. 5 illustrates schematically a cross-section of a sensor with an asymmetrical arrangement of discontinuities within the dielectric membrane, according to an embodiment of the disclosure.
Figure 6A:
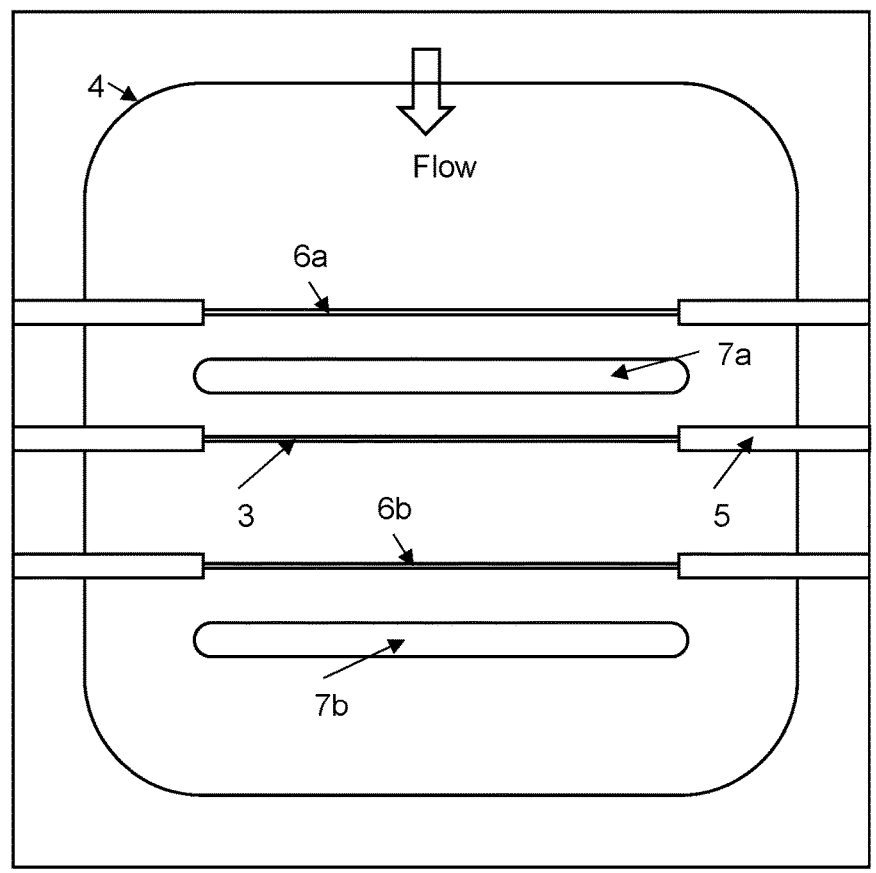
FIG. 6A illustrates schematically a top-view of the sensor of FIG. 5 with an asymmetrical arrangement of discontinuities within the dielectric membrane, according to an embodiment of the disclosure.

FIG. 5 illustrates schematically a cross-section of a sensor with an asymmetrical arrangement of discontinuities within the dielectric membrane, according to an embodiment of the disclosure. FIG. 6A illustrates schematically a top-view of the sensor of FIG. 5 and FIG. 6B illustrates schematically a three-dimensional (3D) top-view of the sensor of FIG. 5.

Figure 6B:
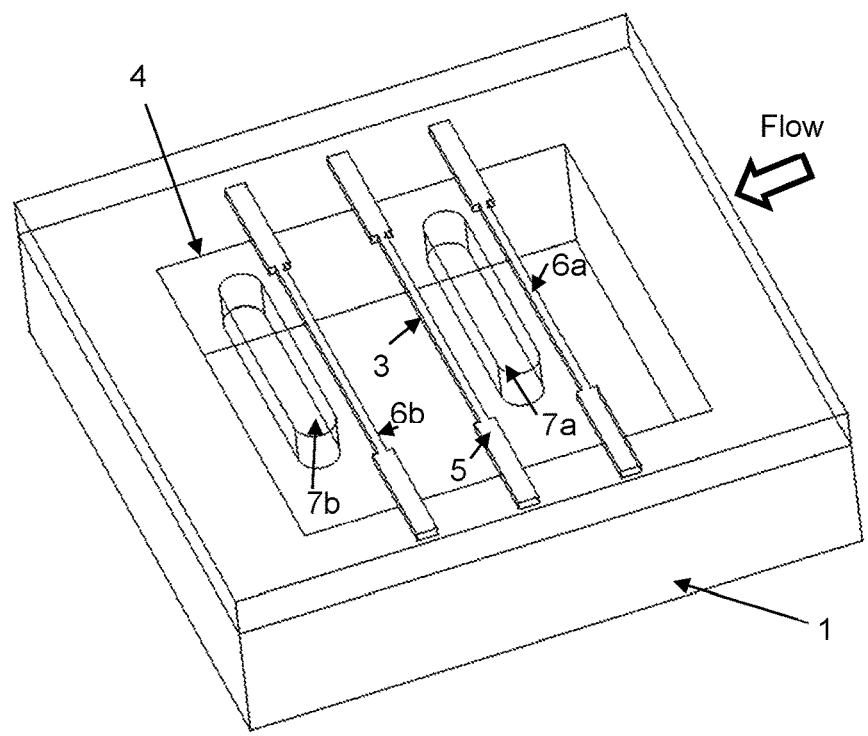
FIG. 6B illustrates schematically a three-dimensional (3D) top-view of the sensor of FIG. 5 with an asymmetrical arrangement of discontinuities within the dielectric membrane, according to an embodiment of the disclosure.

Alternatively, an asymmetrical design is proposed and shown in FIGS. 5, 6A, and 6B. The asymmetrical design can enhance the sensitivity to the composition of the flow (if components of the flow have different thermal conductivity) by enabling a much higher differential change in the temperature between the two sensing elements.

In this embodiment, at least one hole 7a could be placed laterally within the membrane 4 between the heater 3 and the upstream temperature sensing element 6a on one side of the heater 3, and another at least one hole 7b could be placed laterally within the membrane between the downstream temperature sensing element 6b and the edge of the membrane 4 on the other side of the heater 3. In this embodiment, the two holes 7a and 7b or set of holes have similar surface area although may have different surface areas. In this embodiment, the two sensing elements 6a and 6b are identical in terms of dimensions and lateral distance from the heater and could be done in the same fabrication process, for example during CMOS steps prior to membrane etching.

Here 6b operates at higher temperature than 6a even in air (or static flow) when the heater 3 is powered up. If $CO_2$ is present, as the thermal conductivity of the $CO_2$ is smaller than that of air, the temperatures in 6a and 6b would be even more different (e.g. 6b will become even hotter than 6a). The reason for it is that 6a is isolated from the heater through a hole (which has lower thermal conductivity because of the CO2 presence) while no hole is present between it and the edge of the membrane which sits at ambient temperature. This means 6a will become colder than in the case where normal air (with less $CO_2$) would be present. The opposite argument can be given for 6b. 6b has no hole separation between it and the heater but a hole is present between it and the edge of the membrane. In the presence of higher levels of $CO_2$ the hole becomes less thermally conductive allowing the temperature in 6b to rise.

The difference in temperature between the two sensing elements 6b and 6a (the differential signal between 6b and 6a) is in this arrangement proportional with the $CO_2$ concentration. For normal air an offset is present between 6b and 6a. This could be corrected externally by auto zero techniques or simply taken into account in the read-out circuit.

The flow rate or velocity could be measured by the heater itself, by monitoring the change in the temperature for a constant power. Alternatively, the heater 3 could be maintained in a constant temperature or constant resistance modes by modifying the power supplied to the heater element. In this case, one can measure the change in the power due to the flow rate, velocity, volume or mass flow rates.

The heater 3 can also be modulated in temperature to increase selectivity. To differentiate between different components of the fluid (e.g. air, hydrogen, methane, CO2), the heater 3 could be powered up at different temperatures and the results could be assessed against calibrated data or look-up tables stored in memory devices (on-chip or external). The thermal conductivity of these gasses $CO_2$, Hydrogen and methane vary with temperature and the variation is different for each gas present.

Figure 7:
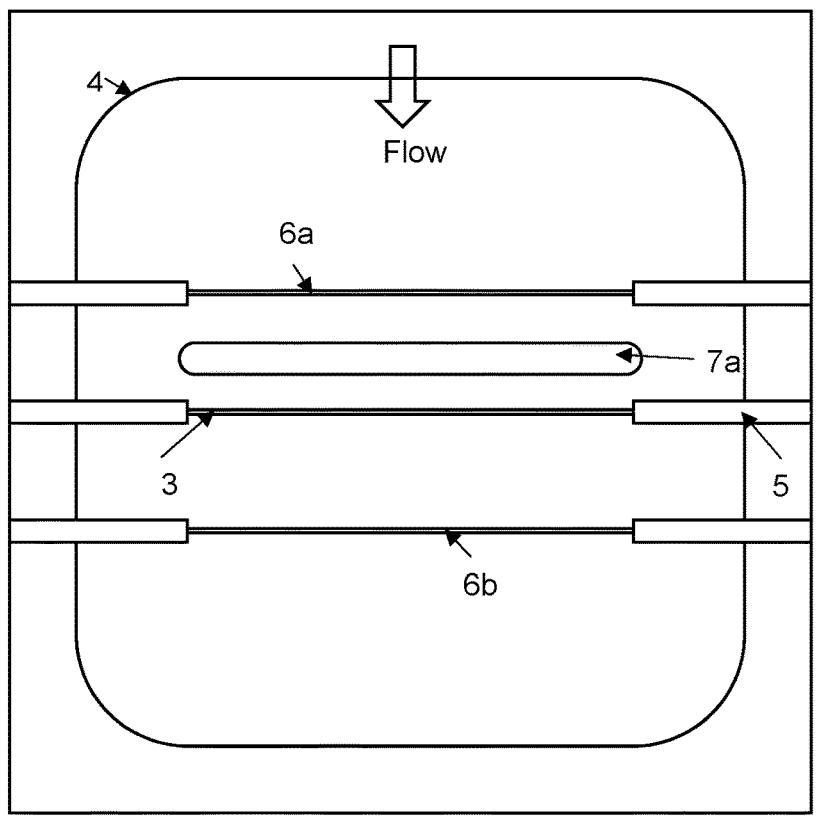
FIG. 7 illustrates schematically a top-view of a sensor with only one discontinuity within the dielectric membrane, according to an alternative embodiment of the disclosure.

FIG. 7 illustrates schematically a cross-section of a sensor with only one discontinuity within the dielectric membrane, according to an alternative embodiment of the disclosure. FIG. 7 shows an alternative, asymmetric design to that shown in FIG. 6. In this embodiment, only one hole is located between the upstream sensing element and the heater. As in the previous embodiment, 6b is hotter than 6a and the difference in temperature between 6b and 6a could be indicative of $CO_2$ or Hydrogen concentration. The structure is simpler than that shown in the embodiment of FIG. 6, however the sensitivity may be greatly reduced.

Figure 8:
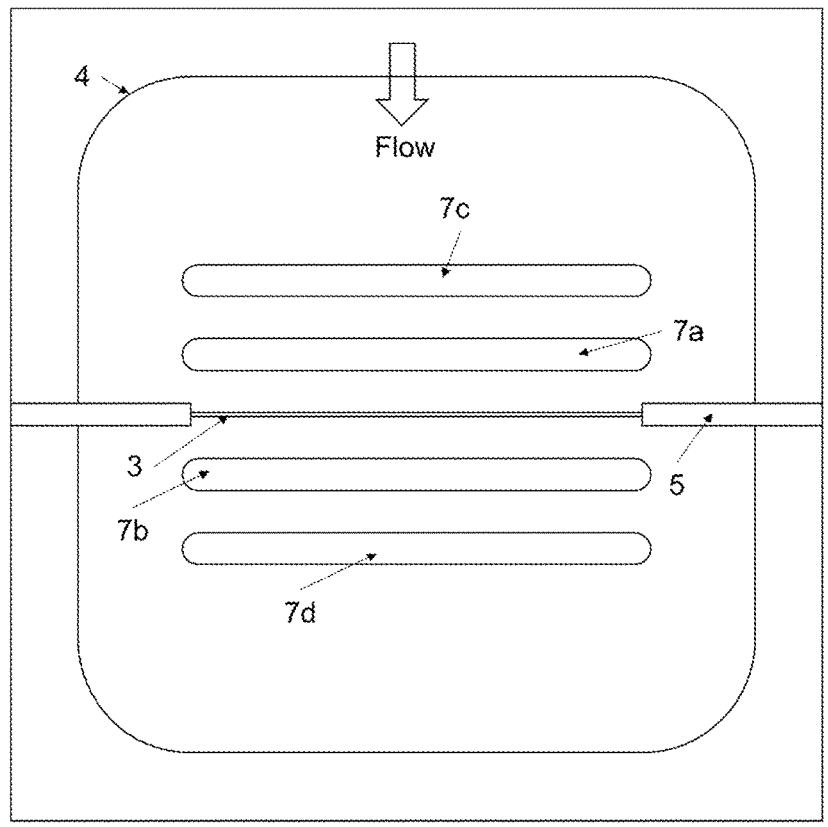
FIG. 8 illustrates schematically a top-view of a sensor where the heater is used as a sensing element, according to an alternative embodiment of the disclosure.

FIG. 8 illustrates schematically a top-view of a sensor where the heater is used as a sensing element, according to an alternative embodiment of the disclosure. FIG. 8 shows a design where more than one hole is present, and the only sensing element is that of the heater itself. The flow rate or velocity could be measured by monitoring the change in the temperature of the heater for a constant power. Alternatively, the heater 3 could be maintained in a constant temperature or constant resistance modes by modifying the power supplied to the heater element. In this embodiment, a user can measure the change in the power due to the flow rate, velocity, volume or mass flow rates.

The heater 3 is then modulated in temperature to detect the composition of the fluid ($CO_2$ concentration in air) against a set of calibrated data.

This design is the simplest as there are no additional sensing elements, but has lower sensitivity and selectivity to the flow components of the flow.

Figure 9:
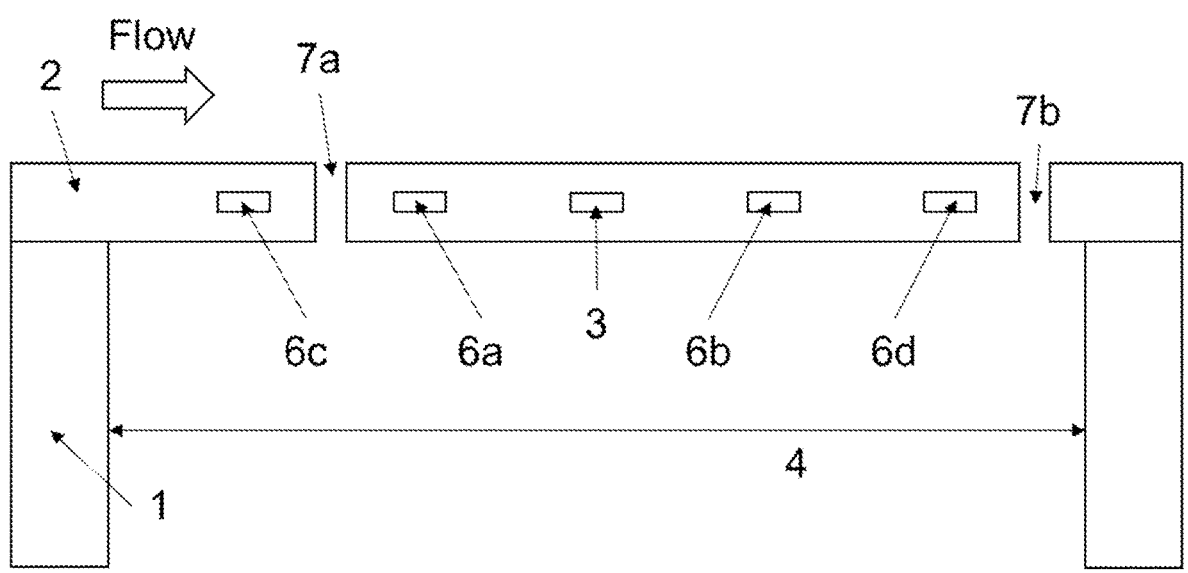
FIG. 9 illustrates schematically a cross-section of a sensor with further sensing elements upstream and downstream of the heating element, according to an alternative embodiment of the disclosure.
Figure 10A:
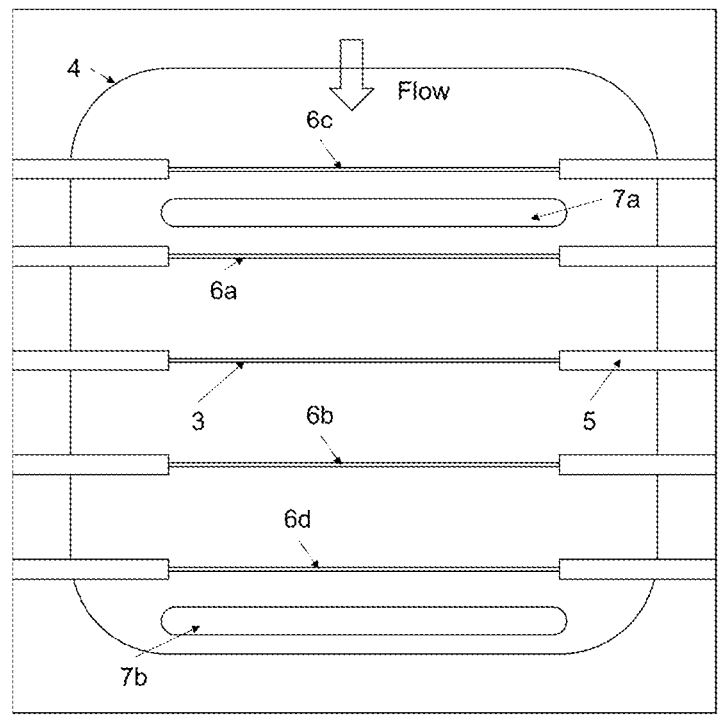
FIG. 10A illustrates schematically a top-view of the sensor of FIG. 9 according to an embodiment of the disclosure.

FIG. 9 illustrates schematically a cross-section of a sensor with further sensing elements upstream and downstream of the heating element, according to an alternative embodiment of the disclosure, and FIG. 10A illustrates schematically a top-view of the sensor of FIG. 9. This is similar to the design shown in FIGS. 5 and 6.

In this embodiment, when compared to sensor shown in FIG. 6, two additional sensing elements (referred to as 6c and 6d) are formed either side of the heater in the upstream (6a) and downstream (6b) position. The differential signal between 6b and 6a is proportional to the flow rate and is less affected by the composition of the flow, as there is no hole between the heater and these sensing elements. The hole 7a is placed laterally within the membrane 4 between the sensing element 6a and the sensing element 6c (in the upstream position), while the hole 7b is placed laterally within the membrane between the sensing element 6d and the edge of the membrane 4 (in the downstream position) on the other side of the heater 3.

Here 6d operates at higher temperature than 6c even in air (or when no flow is present) when the heater 3 is powered up. If $CO_2$ is present, the thermal conductivity of the $CO_2$ is smaller than that of air, the temperatures in 6d and 6c would be even more different (e.g. 6d will become even hotter than 6c). The difference in temperature between the two sensing elements 6d and 6c (the differential signal between the two) is in this arrangement proportional with the CO2 concentration. As already mentioned, the flow rate or velocity can be measured by the difference in temperature between 6b and 6a or by the change in the resistance/power of the heater. By coupling the readouts from the heater 3 and the sensing elements 6a and 6b also the flow directionality can be inferred.

This particular design could also be used to measure the "no flow" (or zero flow or static flow) condition. In this case, because of symmetry, the signal difference (as temperature or voltage or resistance difference) between the sensing elements 6b and 6a should be zero. However there is still an offset in normal air (or no flow) between 6d and 6c. This could be corrected to zero by the read-out circuit for normal air. When $CO_2$ is present, even if no flow occurs, the differential signal difference (quantified as temperature or voltage or resistance difference) between 6d and 6c increases linearly with the $CO_2$ concentration. This could be useful to measure the $CO_2$ concentration in air, for example, for air quality applications.

Figure 10B:
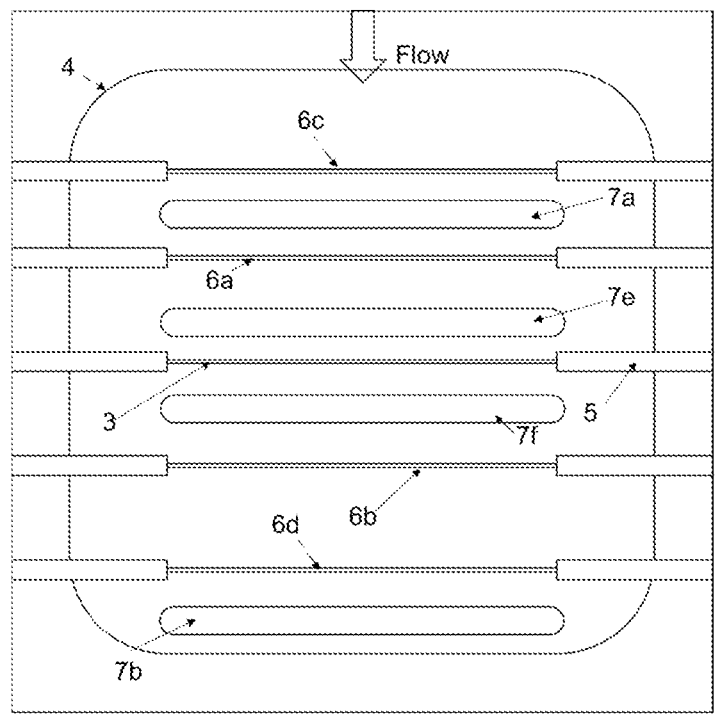
FIG. 10B illustrates schematically a top-view of an alternative sensor similar to that shown in FIG. 9 but with additional discontinuities, according to an embodiment of the disclosure.

FIG. 10B illustrates schematically a top-view of an alternative sensor similar to that shown in FIG. 9 but with additional discontinuities, according to an embodiment of the disclosure. FIG. 10b shows a design similar to FIG. 10a, with two additional holes 7e and 7f on either side of the heater 3. These additional holes allow a greater thermal isolation between the elements 6a and 6b and so allow a higher measurement sensitivity.

Figure 11:
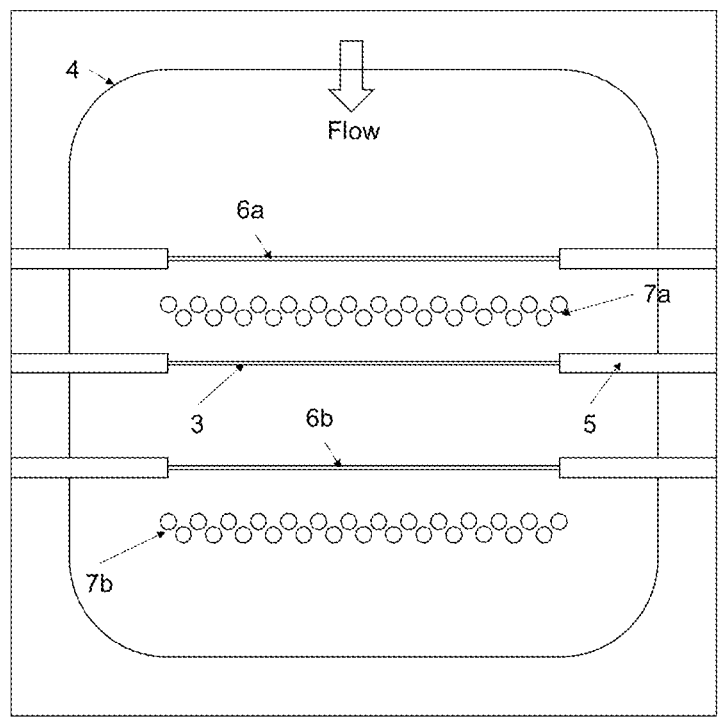
FIG. 11 illustrates schematically a top-view of a sensor similar to that shown in FIG. 6 with an array of smaller holes within the dielectric membrane, according to an alternative embodiment of the disclosure.

FIG. 11 illustrates schematically a top-view of a sensor similar to that shown in FIG. 6 with array of smaller holes or perforations within the dielectric membrane, according to an alternative embodiment of the disclosure. FIG. 11 is similar to the design of FIG. 6 but a number of small holes 7a and 7b are formed upstream and downstream respectively.

This design helps in ensuring that the membrane strength is not compromised during manufacturing or during operation. In the case of the fluid being a liquid (rather than gas) this design could help to also avoid trapping liquid under the membrane. The small holes (e.g. with a diameter of micrometres) could also be more easily processed during the device fabrication without damaging the internal layers of the membrane due to for example over etching. The geometrical arrangement in one or several rows of holes reduces the thermal conduction through the membrane but without significantly affecting the mechanical stability and the manufacturability of the membrane structure. The presence of the holes allows the equalising of the pressure on both sides of the membrane and allows higher membrane deflections to minimise the strain in the membrane and thus improve the long-term reliability of the device. The holes also avoid build-up of a differential pressure between top and bottom of the membrane that during packaging/assembly may lead the device to fail. The elongate slots of any other embodiment may be interchanged with the small holes or perforations of the thing embodiment.

Figure 12:
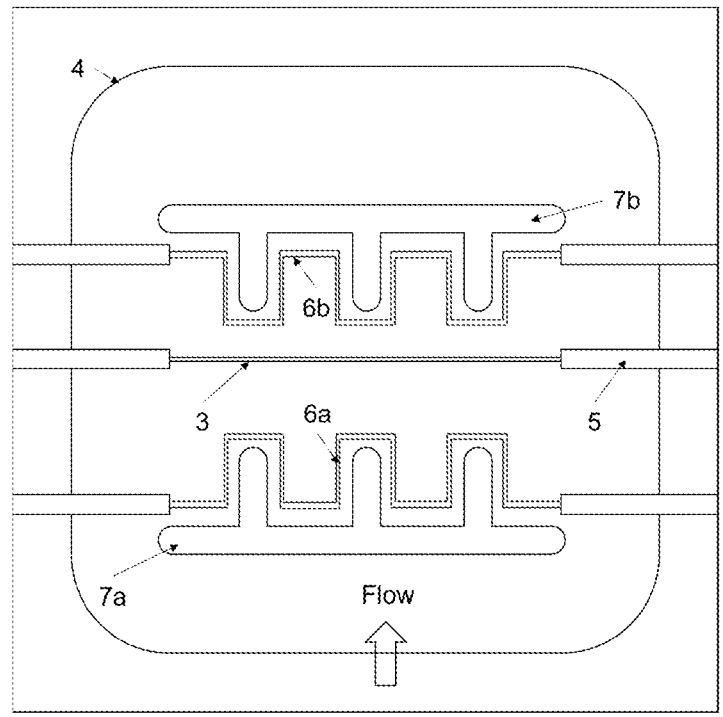
FIG. 12 illustrates schematically a top-view of a sensor with a symmetrical arrangement of holes of non-standard shapes, according to an alternative embodiment of the disclosure.

FIG. 12 illustrates schematically a top-view of a sensor with a symmetrical arrangement of holes of non-standard shapes, according to an alternative embodiment of the disclosure. FIG. 12 shows a symmetrical design where the holes and the sensing elements could have different shapes (non-standard shapes). In this embodiment shown, the sensing elements have a meander shape and the holes have a corresponding, matching shape. This design increases the length of the sensing element, which increases accuracy and easiness of signal processing. The matching shape of the holes help to reduce the heat losses through the membrane.

Figure 13:
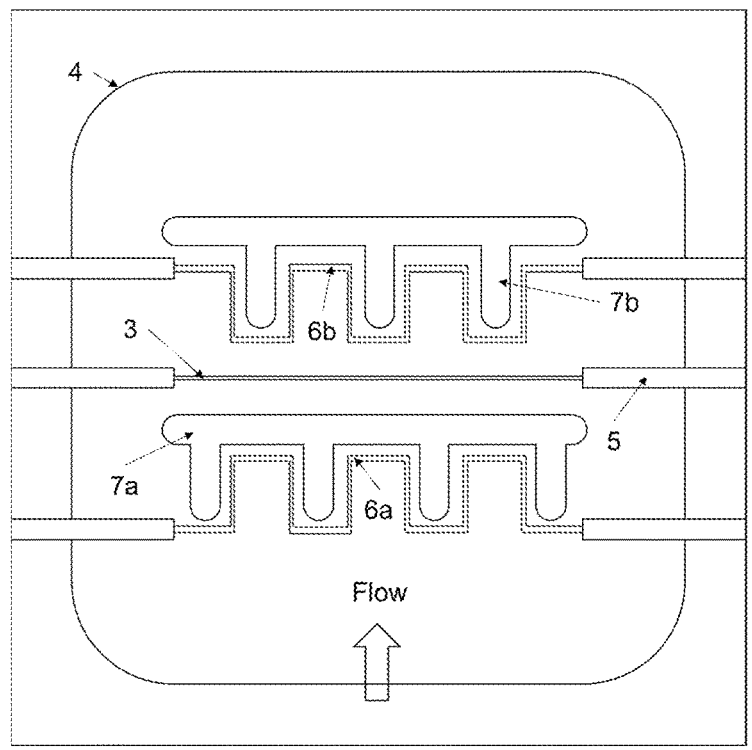
FIG. 13 illustrates schematically a top-view of a sensor similar to that shown in FIG. 6 with an arrangement of holes of non-standard shapes within the dielectric membrane, according to an alternative embodiment of the disclosure.

FIG. 13 illustrates schematically a top-view of a sensor similar to that shown in FIG. 6 with an arrangement of holes of non-standard shapes within the dielectric membrane, according to an alternative embodiment of the disclosure. The design example in FIG. 13 has sensing elements and holes with the same shapes as those shown in FIG. 12 but this time uses an asymmetrical arrangement, similar to that shown in FIG. 6. This design could further improve the sensitivity and the sensing elements have a higher resistance due to the meander shape, which could be more advantageous for the read-out circuitry.

Figure 14:
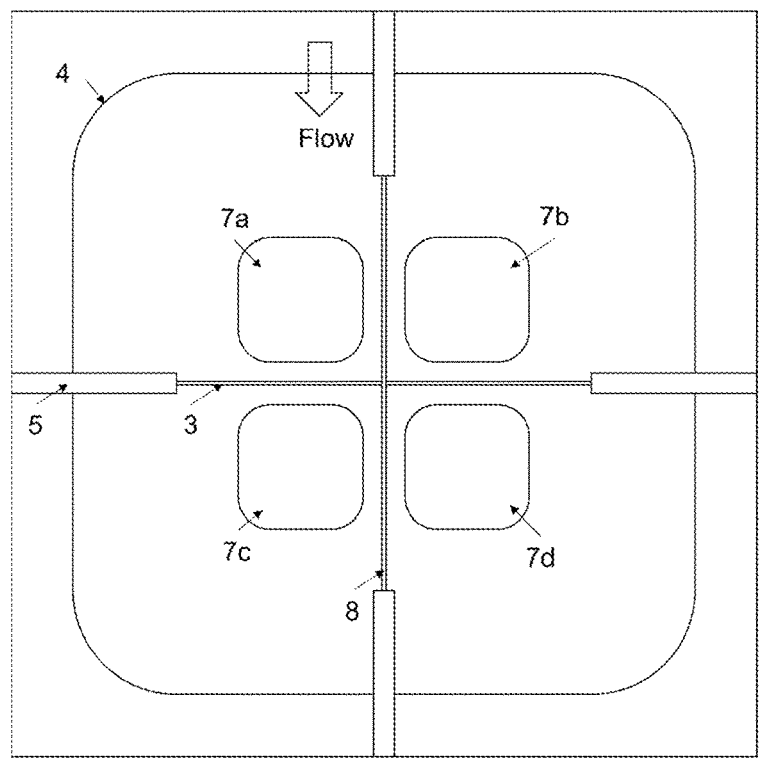
FIG. 14 illustrates schematically a top-view of a sensor with an additional heater, according to an alternative embodiment of the disclosure.

FIG. 14 illustrates schematically a top-view of a sensor with an additional heater, according to an alternative embodiment of the disclosure. FIG. 14 shows a symmetrical design with one additional/further heater or heating element (hotwire), 8 to discriminate between the presence and the parameters of the flow and the composition of the fluid. The further heating element extends in a direction parallel to direction of flow through the sensor. The two heaters 3 and 8 could be operated in pulse mode at different times. The heater 3 could be operated to sense the flow parameters, such as flow rate, velocity, mass or volume flow rates, by measuring its resistance in the presence of flow (or by monitoring the temperature/power of a sensing element or the differential signal of a pair of sensing elements—not shown) and the second heater 8 could be used to enable the detection of different fluid components (flow composition). The first heater 3, which contains a hot wire, has a direction that is orthogonal to the direction of the flow to enhance the sensitivity to flow rate/velocity, while the second heater is aligned to the flow direction to be less affected by the flow rate/velocity and instead measure the composition of the fluid. The two heaters may be made of different metal layers (e.g. Al, Tungsten, Copper, Titanium, Platinum etc.) available in the fabrication process (e.g. CMOS process). Around the second heater a pair of sensing elements and holes could be provided to enhance the detection of the fluid components. In FIG. 14 the holes are symmetrically placed around the two heaters.

Figure 15:
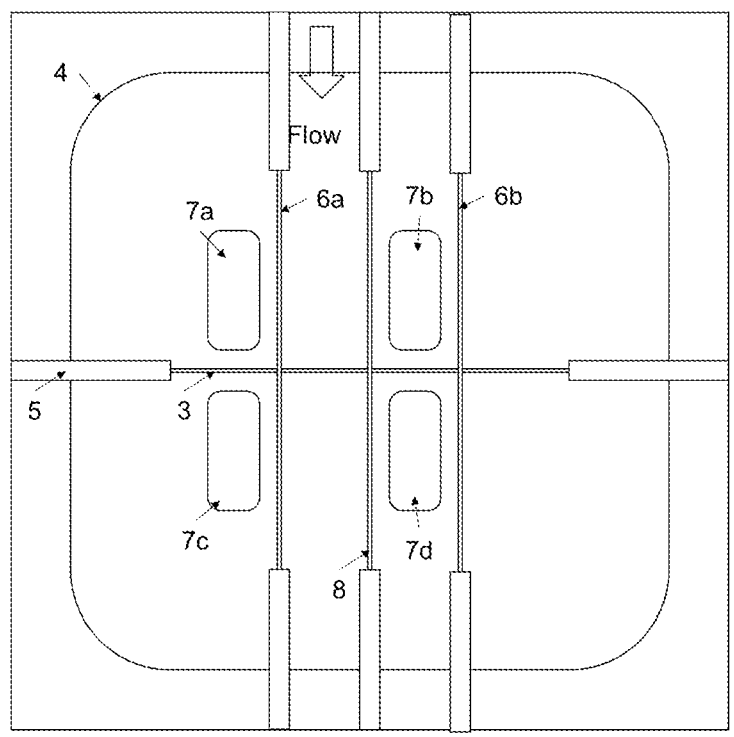
FIG. 15 illustrates schematically a top-view of a sensor similar to that shown in FIG. 14 with an asymmetrical arrangement of holes within the dielectric membrane, according to an alternative embodiment of the disclosure.

FIG. 15 illustrates schematically a top-view of a sensor similar to that shown in FIG. 14 with an asymmetrical arrangement of holes within the dielectric membrane, according to an alternative embodiment of the disclosure. FIG. 15 also shows a two heater arrangement with a similar scope to that described in the embodiment shown in FIG. 14. The sensing elements 6a, 6b in this embodiment are parallel due to the direction of flow and to the further heating element 8. This time an asymmetrical design is proposed to enhance the sensitivity to detection of the fluid components. When heater 8 is operated, 6a will be hotter than 6b and the temperature difference between 6a and 6b will be proportional with the $CO_2$ concentration. Given that the heater 8 and the sensing elements 6a and 6b are aligned to the flow, the temperature difference between 6a and 6b due to the flow rate will be less significant than in the case where these structures heater 8, sensing elements 6a and 6b would have been placed perpendicular to the flow direction. In this respect this particular design offers high sensitivity to the flow composition and is able to discriminate more effectively between changes in temperature due to flow or concentration of fluid components that have different thermal conductivities.

Figure 16:
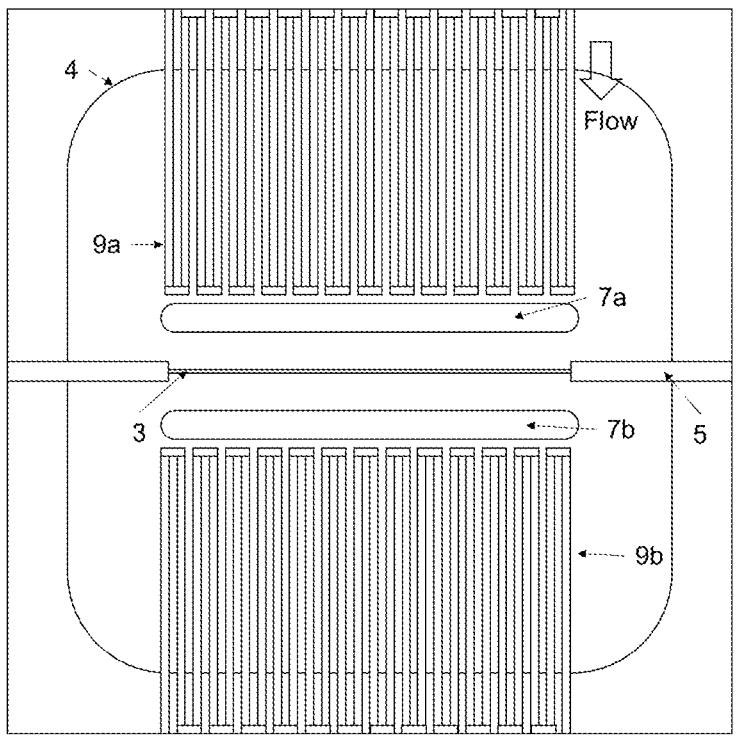
FIG. 16 illustrates schematically a top-view of a sensor with thermopiles placed upstream and downstream of the heating element, according to an alternative embodiment of the disclosure.

FIG. 16 illustrates schematically a top-view of a sensor with thermopiles placed upstream and downstream of the heating element, according to an alternative embodiment of the disclosure. FIG. 16 shows a symmetrical design with a heater 3 and two holes 7a and 7b. Thermopiles 9a and 9b are placed upstream and downstream in the direction of the flow. The thermopiles are relative temperature sensors that can sense a difference in temperatures between a hot junction and a cold junction and translate them into voltage changes without the need of any external power supply. The hot junctions of 9a and 9b are placed closer to the holes 7a and 7b respectively, while the cold junctions are placed outside the membrane above the semiconductor substrate. The thermopiles therefore each measure a temperature difference between the dielectric membrane and the dielectric region above the semiconductor substrate. The differential voltage signal between the hot junctions of the thermopiles 9b and 9a depends on the thermal conductivity of the fluid. This assumes that the cold junctions will stay at the same temperature.

Each of the thermopiles shown comprises one or more thermocouples connected in series. Each thermocouple is formed by joining together two dissimilar materials (e.g. two metals, two semiconductors, one metal and one semiconductor). The thermocouple materials may comprise a metal such as aluminium, tungsten, titanium or combination of those or any other metal available in the process. Alternatively, the thermocouple materials may comprise thermocouples based on n-type and p-type silicon or polysilicon or combinations of metals and semiconductors. The voltage across the thermopile is directly proportional to the temperature difference between the hot and cold junctions, the Seebeck coefficient of the thermocouple and the number of thermocouples in series.

Figure 17:
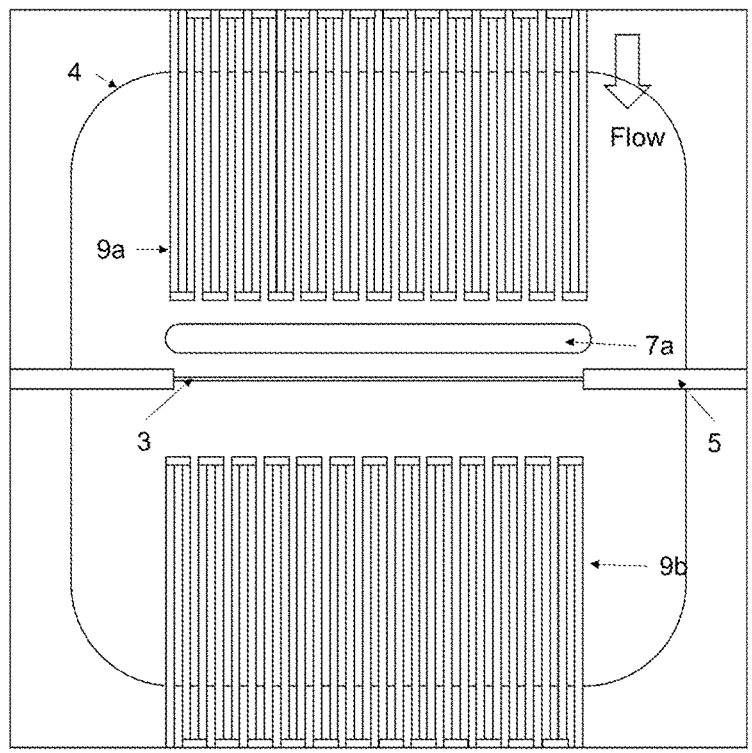
FIG. 17 illustrates schematically a top-view of a sensor similar to that shown in FIG. 16 with a single hole upstream of the heating element, according to an alternative embodiment of the disclosure.

FIG. 17 illustrates schematically a top-view of a sensor similar to that shown in FIG. 16 with a single hole upstream of the heating element, according to an alternative embodiment of the disclosure. FIG. 17 shows an asymmetrical design with only one hole 7a placed upstream in the direction of the flow. The hot junction of 9a will be at lower temperature than the hot junction of 9b. This imbalance will grow for higher concentrations of a fluid component with lower thermal conductivity (e.g. concentration of $CO_2$ in air). This arrangement offers better sensitivity to the flow composition compared to the symmetrical design shown in FIG. 16.

Figure 18:
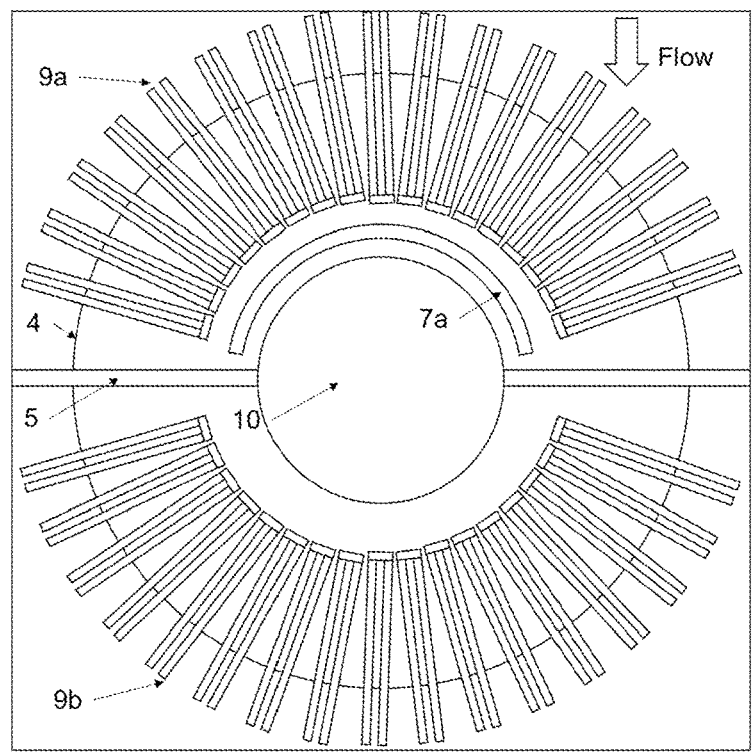
FIG. 18 illustrates schematically a top-view of a sensor with a circular membrane and corresponding shapes for the heater, holes, and thermopiles, according to an alternative embodiment of the disclosure.
Figure 19:
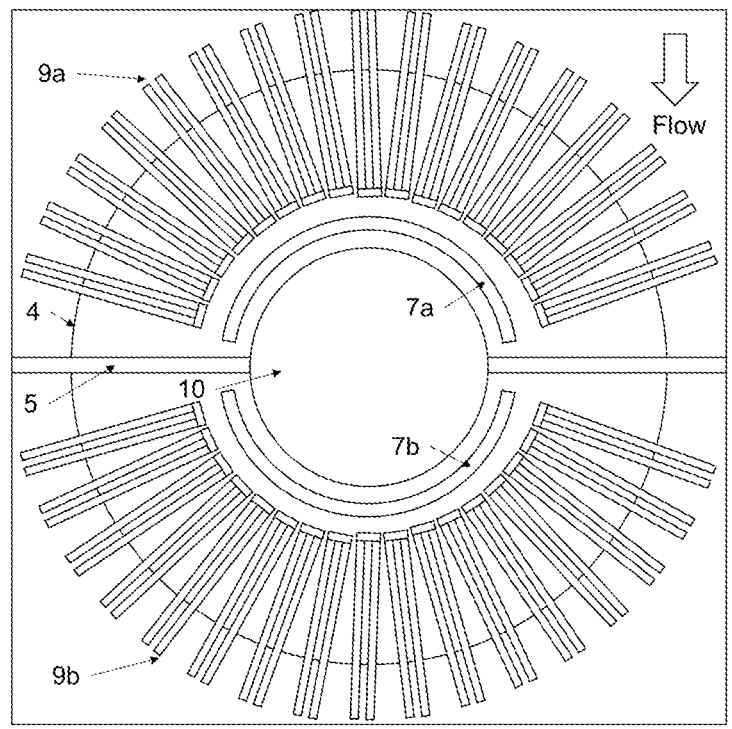
FIG. 19 illustrates schematically a top-view of a sensor similar to that shown in FIG. 18 with a symmetrical arrangement of holes, according to an alternative embodiment of the disclosure.

FIG. 18 illustrates schematically a top-view of a sensor with a circular membrane and corresponding arc shapes for the heater, holes, and thermopiles, according to an alternative embodiment of the disclosure and FIG. 19 illustrates schematically a top-view of a sensor similar to that shown in FIG. 18 with a symmetrical arrangement of holes.

FIG. 18 and FIG. 19 show asymmetrical and symmetrical devices respectively, with circular membranes and corresponding matching shapes for the heater 10, holes 7a and 7b and thermopiles 9a and 9b. The heater 10 is a microhotplate, in this case powered through the metal tracks 5. These arrangements benefit from a better use of the membrane area and higher thermal performance, but their design is more complicated than that shown in FIG. 16 and FIG. 17.

Figure 20:
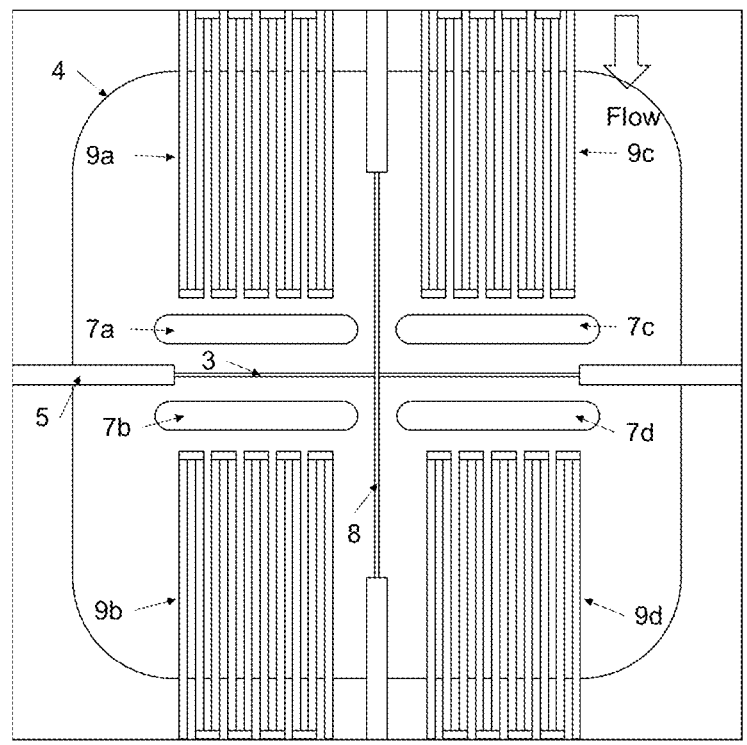
FIG. 20 illustrates schematically a top-view of a sensor with four holes and four thermopiles, according to an alternative embodiment of the disclosure.
Figure 21:
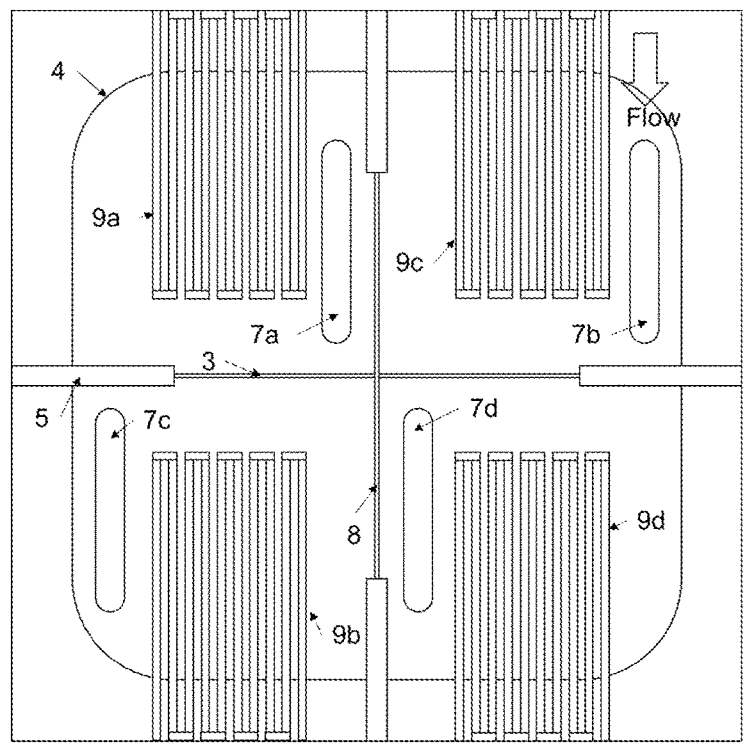
FIG. 21 illustrates schematically a top-view of a sensor similar to that shown in FIG. 20 with an asymmetrical arrangement of holes, according to an alternative embodiment of the disclosure.

FIG. 20 illustrates schematically a top-view of a sensor with four holes and four thermopiles, according to an alternative embodiment of the disclosure; and FIG. 21 illustrates schematically a top-view of a sensor similar to that shown in FIG. 20 with an asymmetrical arrangement of holes.

FIGS. 20 and 21 show different symmetrical and asymmetrical designs (respectively) using 4 holes and 4 thermopiles. Using differential and sum signals between different sets of thermopiles it is possible to differentiate between flow properties such as flow rate or velocity and composition of the flow based on thermal conductivity differences between different components of the flow. For example, referring to the embodiment in FIG. 21, and assuming the temperature of the cold junctions for all thermopiles is the same, $T9a+T9c-(T9b+T9d)$ could give the flow properties, while $T9c+T9b-(T9a+T9d)$ can give a signal based on the thermal conductivity of the different components of the fluid. $T9x$ represents the hot junction temperature of $9x$ thermopile. Note that the signal is measured as voltage differences and depends on the Seebeck coefficient and the number of thermocouples in series for each thermopile.

To minimise the effect of different cold junction temperatures, the cold junctions of all the thermopiles shown in FIG. 15 to FIG. 21 can be electrically or thermally connected together through metallization outside on the membrane or on the edge of the membrane. The cold junctions of all these thermopiles could be connected to ground and used as a reference potential.

Figure 22:
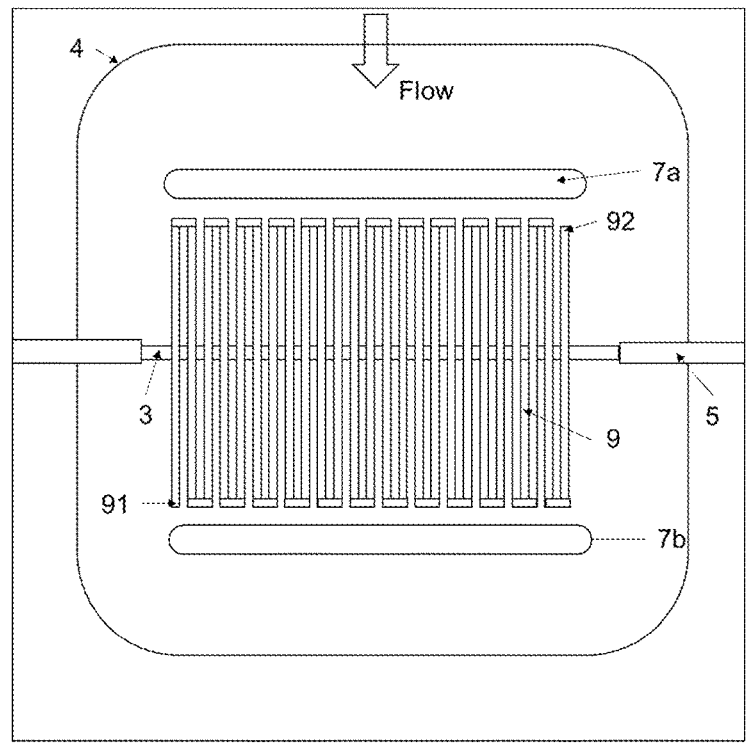
FIG. 22 illustrates schematically a top-view of a sensor with one thermopile placed across the heating element, according to an alternative embodiment of the disclosure.

FIG. 22 illustrates schematically a top-view of a sensor with one thermopile placed across the heating element, according to an alternative embodiment of the disclosure. FIG. 22 shows another embodiment where a thermopile 9 is placed symmetrically around/across the heater 3. The heater is shown here as a hotwire placed perpendicularly to the direction of the flow. The hot junction of the thermopile 91 can be one side of the heater 3 and the cold junction 92 on the other side of the heater, both within the membrane 4 at a certain distance from the edge of the membrane. Holes 7a and 7b could be placed symmetrically within the membrane in the space between the thermopile and the edge of the membrane. The thermopile measures a temperature differential across the heating element. The difference in voltage (proportional with the different in temperature) between the hot junction 91 and cold junction 92 is indicative of the flow properties. The heater 3 could be modulated in temperature and the thermopile voltage (the voltage drop between the hot junction 91 and cold junction 92) could be assessed against a calibrated data to indicate the composition of the flow. This could be also correlated to a measurement of the resistance of the heater 3.

Figure 23:
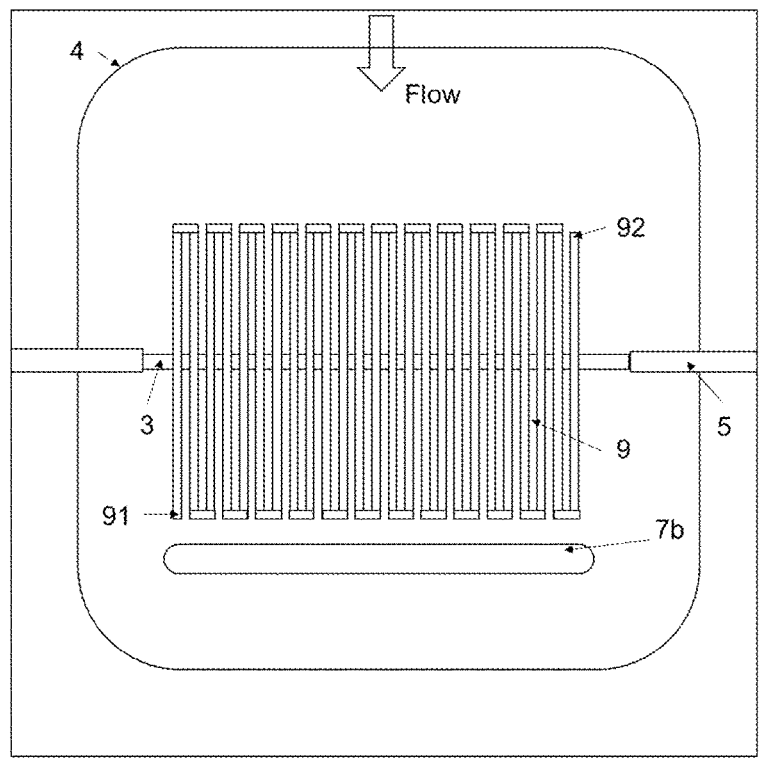
FIG. 23 illustrates schematically a top-view of a sensor similar to that shown in FIG. 22 with a single hole downstream of the heating element, according to an alternative embodiment of the disclosure.

FIG. 23 illustrates schematically a top-view of a sensor similar to that shown in FIG. 22 with a single hole downstream of the heating element, according to an alternative embodiment of the disclosure. FIG. 23 shows a similar structure to that shown in FIG. 22 with the difference that holes are asymmetrically placed. Here a single hole is shown in the downstream position.

This helps to enhance the sensitivity/selectivity to the different components of the flow. If a higher concentration of $CO_2$ is present the hot junction 91 would operate hotter than for example if only normal air is present in the flow. The heater 3 could be modulated in temperature and the thermopile voltage (the voltage drop between the hot junction 91 and cold junction 92) could be used to discriminate between the flow properties and the composition of the flow and/or to enhance the sensitivity/selectivity to the flow composition (e.g. $CO_2$ concentration in air or Hydrogen concentration)

Figure 24:
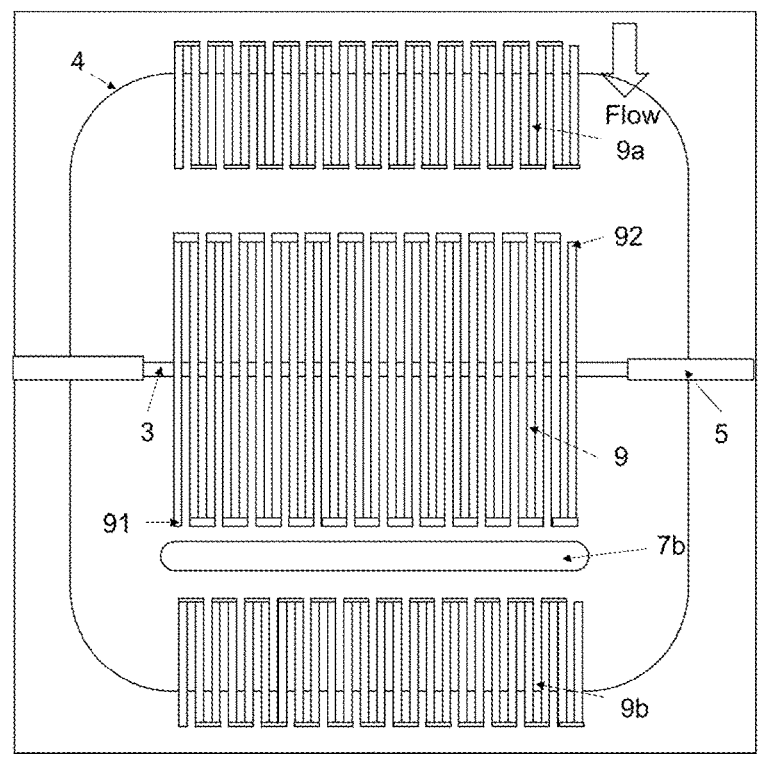
FIG. 24 illustrates schematically a top-view of a sensor similar to that shown in FIG. 22 with two additional thermopiles, according to an alternative embodiment of the disclosure.

FIG. 24 illustrates schematically a top-view of a sensor similar to that shown in FIG. 22 with two additional thermopiles, according to an alternative embodiment of the disclosure. FIG. 24 shows a similar structure to that shown in FIG. 23 with two additional thermopiles (9a upstream and 9b downstream) placed either side of the heater and having the cold junctions placed outside the membrane. This embodiment operates similarly to the embodiment of FIG. 7. The first thermopile 9 could be used to measure the flow direction and flow properties such as flow rate or velocity while the difference in voltage between the hot junctions of the upstream and downstream thermopiles could be used to measure the concentrations of different components of the flow. The design has more parameters to measure compared to the previous design in FIG. 23, but is more complicated and can have additional thermal loses through the thermopiles themselves.

Figure 25:
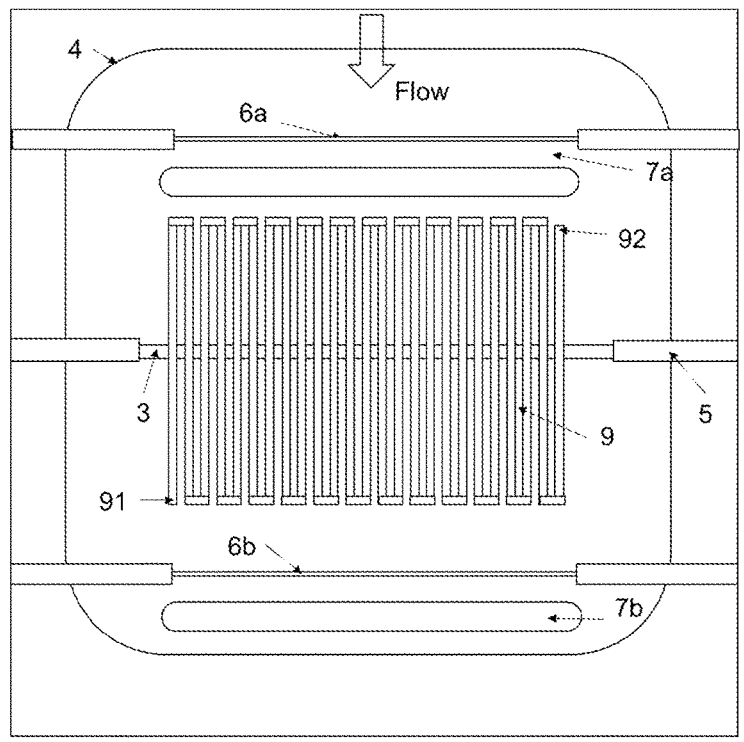
FIG. 25 illustrates schematically a top-view of a sensor with thermopiles and resistive temperature detectors, according to an alternative embodiment of the disclosure.

FIG. 25 illustrates schematically a top-view of a sensor with thermopiles and resistive temperature detectors, according to an alternative embodiment of the disclosure. FIG. 25 shows a combination design where the sensing elements are both a thermopile 9 and two resistive temperature detectors or diodes, one upstream 6a and one downstream 6b. This device has lower thermal losses than the one shown in FIG. 23 as there are no additional thermopiles through which heat can dissipate. In addition the asymmetrical presence of the holes 7a and 7b helps to increase the sensitivity/selectivity to the flow composition (in a similar way to the effect described in relation to the embodiment shown in FIG. 6).

Figure 26:
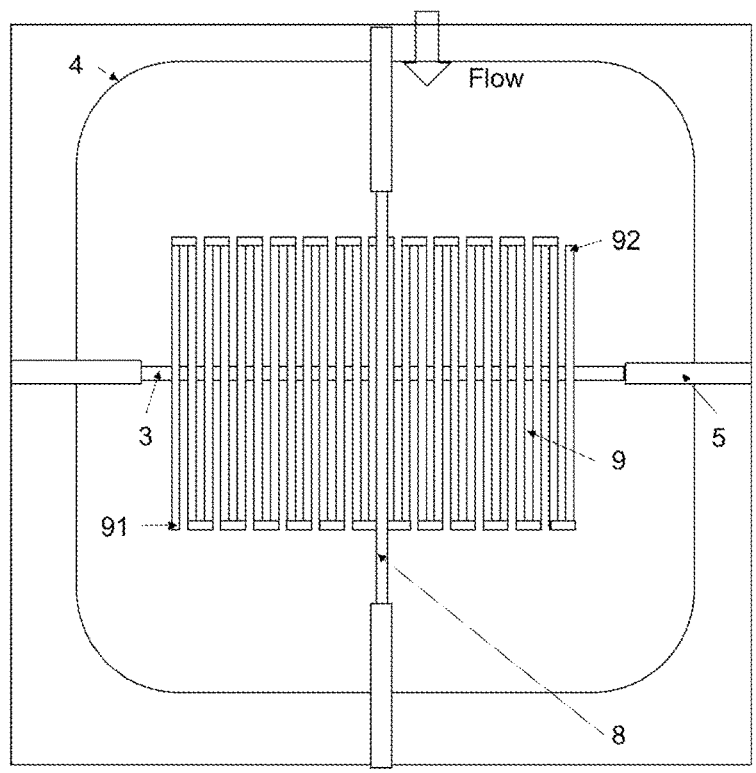
FIG. 26 illustrates schematically a top-view of a sensor with a second heating element perpendicular to a first heating element, according to an alternative embodiment of the disclosure.

FIG. 26 illustrates schematically a top-view of a sensor with a second heating element perpendicular to a first heating element, according to an alternative embodiment of the disclosure. FIG. 26 shows a two heater design with a first heater 3 placed perpendicular to the direction of the flow and the second heater 8 placed in a direction aligned to the flow direction. The two heaters are not connected physically or electrically and can be for example made of different metal layers. A thermopile 9, (also made in different layers than the heaters 3 and 8) can be placed symmetrically around or across both the heaters. The hot junction 91 can be placed on one side of the first heater 3 and the cold junction 92 on the other side of the first heater 3, both within the membrane at a certain distance from the heater and the edge of the membrane. The heaters could be operated in pulse mode at different times. The first heater 3, perpendicular to the direction of the flow could be operated to sense the flow properties, such as flow rate, velocity, mass or volume flow rates, by measuring the voltage drop of the thermopile, while the second heater 8, aligned to the flow could be operated to sense the flow composition by measuring the voltage drop of the thermopile, when the heater 3 is off. Both the first 3 and/or the second heater 8 could be modulated in temperature to increase the accuracy of the measurements and improve sensitivity/selectivity to different components of the flow.

Figure 27:
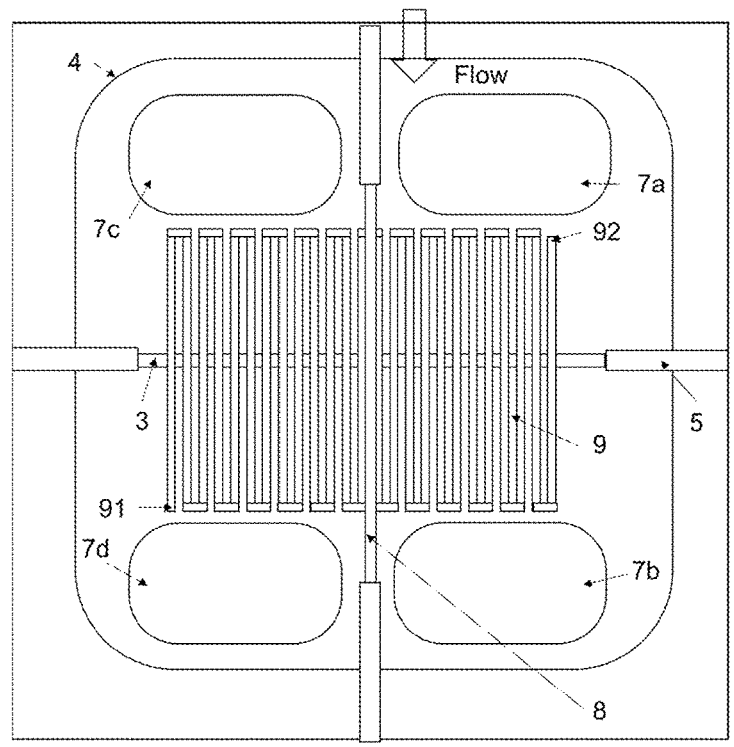
FIG. 27 illustrates schematically a top-view of a sensor similar to that shown in FIG. 26 with a symmetrical arrangement of holes, according to an alternative embodiment of the disclosure.

FIG. 27 illustrates schematically a top-view of a sensor similar to that shown in FIG. 26 with a symmetrical arrangement of holes, according to an alternative embodiment of the disclosure. FIG. 27 shows a two heater design with a symmetrical design of holes 7a and 7c upstream, 7b and 7d downstream). Here the holes are provided to reduce the thermal losses, reduce the thermal mass and enhance sensitivity/selectivity to different components of the flow.

Figure 28:
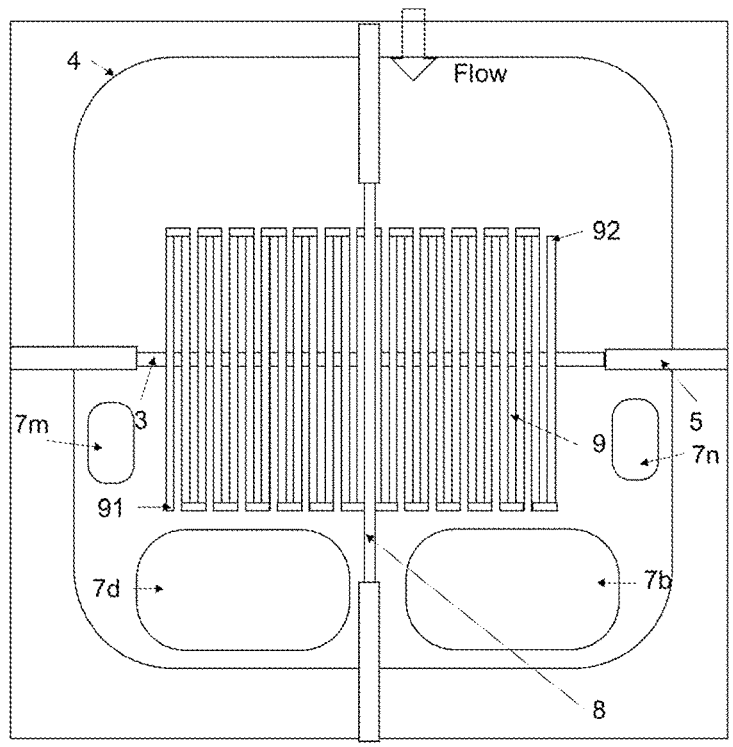
FIG. 28 illustrates schematically a top-view of a sensor similar to that shown in FIG. 27 with an asymmetrical arrangement of holes downstream of the heating element, according to an alternative embodiment of the disclosure.

FIG. 28 illustrates schematically a top-view of a sensor similar to that shown in FIG. 27 with an asymmetrical arrangement of holes downstream of the heating element, according to an alternative embodiment of the disclosure. In FIG. 28 the holes (7b, 7d, 7m, and 7n) are placed asymmetrically (here shown in a downstream position) to provide a larger differential signal on the thermopile (compared to the design in FIG. 27) and thus provide a further enhancement in the sensitivity/selectivity to different components of the flow.

Figure 29:
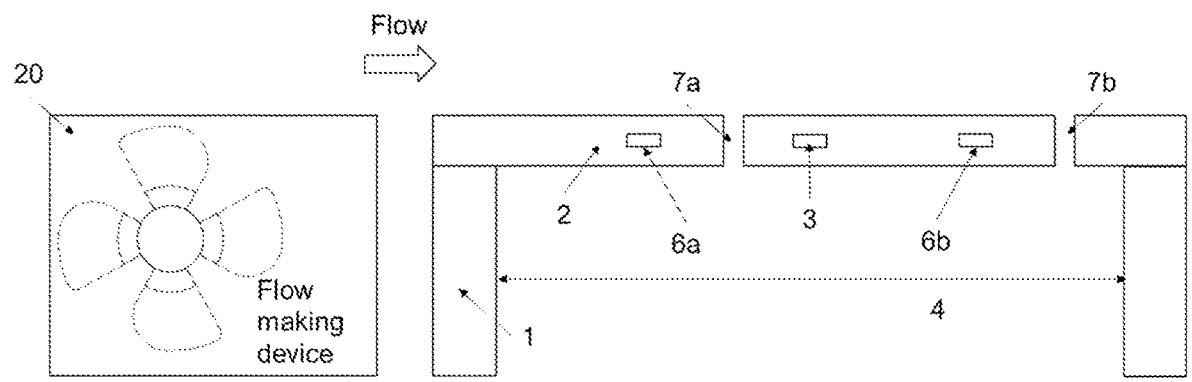
FIG. 29 illustrates schematically a cross-section of a sensor with a flow mechanism for controlling or producing a fluid flow, according to an alternative embodiment of the disclosure.

FIG. 29 illustrates schematically a top-view of a sensor with a flow mechanism 20 for controlling or producing a fluid flow, according to an alternative embodiment of the disclosure. In FIG. 29 a flow making device 20 is provided adjacent to the flow/thermal conductivity sensor to create or manipulate flow (e.g. micro-pump, micro-fan or an additional heater that creates a temperature gradient and flow via thermophoresis or thermodiffusion). The flow making device 20 may also be a valve-type device. The valve-type device may be fully closed to bring the system in a condition of zero flow, may be partly closed to reduce the speed of flow, or may be left fully open not to manipulate the flow. In case of the valve-type device fully closed, a pressure would build across the valve-type device, so that when the valve-type device is opened a flow would be generated with velocity proportional to the pressure build across the valve type device while it was closed. The device 20 could serve to enhance the signal/accuracy indicative of the composition of the fluid present (based on the thermal conductivity difference of different components of the flow enhanced by the flow convection). For example, the flow could enhance the differential signal between the sensing elements 6b and 6a, which gives information about the flow composition. The flow rate could be calibrated by evaluating the resistance change of the heater 3.

Figure 30:
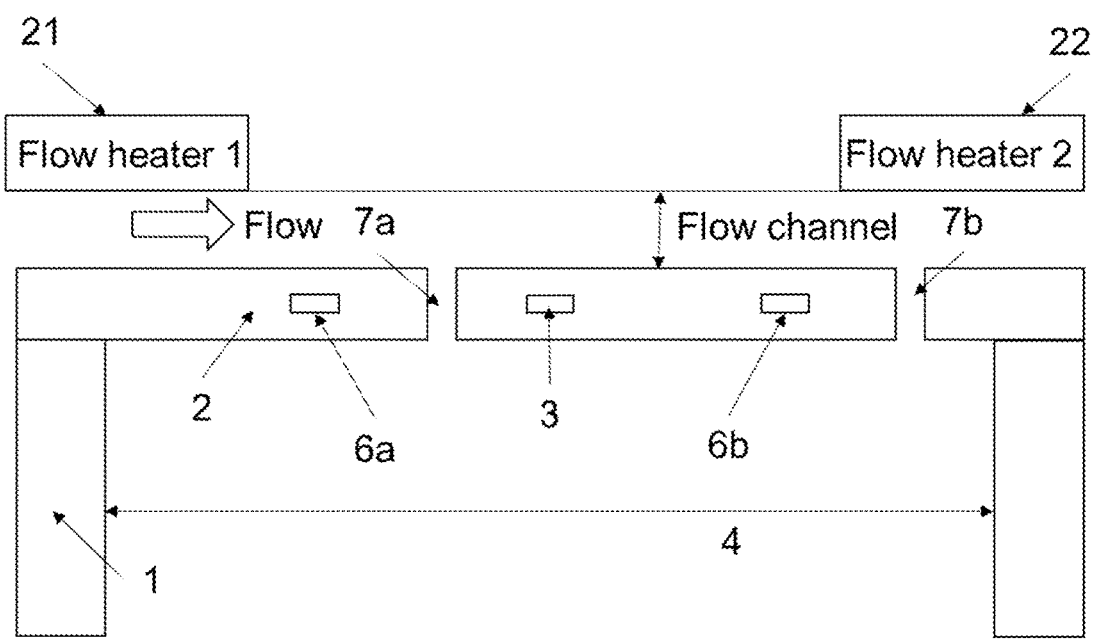
FIG. 30 illustrates schematically a cross-section of a sensor with flow heaters for controlling or producing a temperature gradient, according to an alternative embodiment of the disclosure.

FIG. 30 illustrates schematically a cross-section of a sensor with flow heaters for controlling or producing a temperature gradient, according to an alternative embodiment of the disclosure. In FIG. 30 we show two additional heaters 21, 22, that could be in the form of MEMS micro-hotplates, placed within a channel, and formed optionally within a manifold. The two additional heaters 21, 22 may also be in form of coils wrapped around the flow channel. The flow heaters act as a flow mechanism. The flow heaters 1 and 2 operate at different temperatures and create a controllable temperature gradient in the channel which results in a flow at the surface of the flow/thermal conductivity sensor. As in the previous case, the flow could enhance the differential signal between 6b and 6a, which gives information about the flow composition. The flow rate could be calibrated by evaluating the resistance change of the heater 3.

The designs shown in FIGS. 29 and 30 are particularly useful in a no flow or static environment condition. The no flow condition could be detected by the flow sensor or by using a device similar to the one in FIG. 10. To enhance the accuracy for detection of different components and their relative concentration in the fluid, the flow making device (in FIG. 29) or the flow heaters (in FIG. 30) could be turned on. Such devices could be used to sense the CO2 percentage/ppm in static air more accurately. The temperature of the heater 3 could also be modulated to increase selectivity. To differentiate between different components of the fluid (e.g. air, hydrogen, methane, CO2), the heater 3 could be powered up at different temperatures and the results could be assessed against calibrated data or look-up tables stored in memory devices (on-chip or external).

Figure 31:
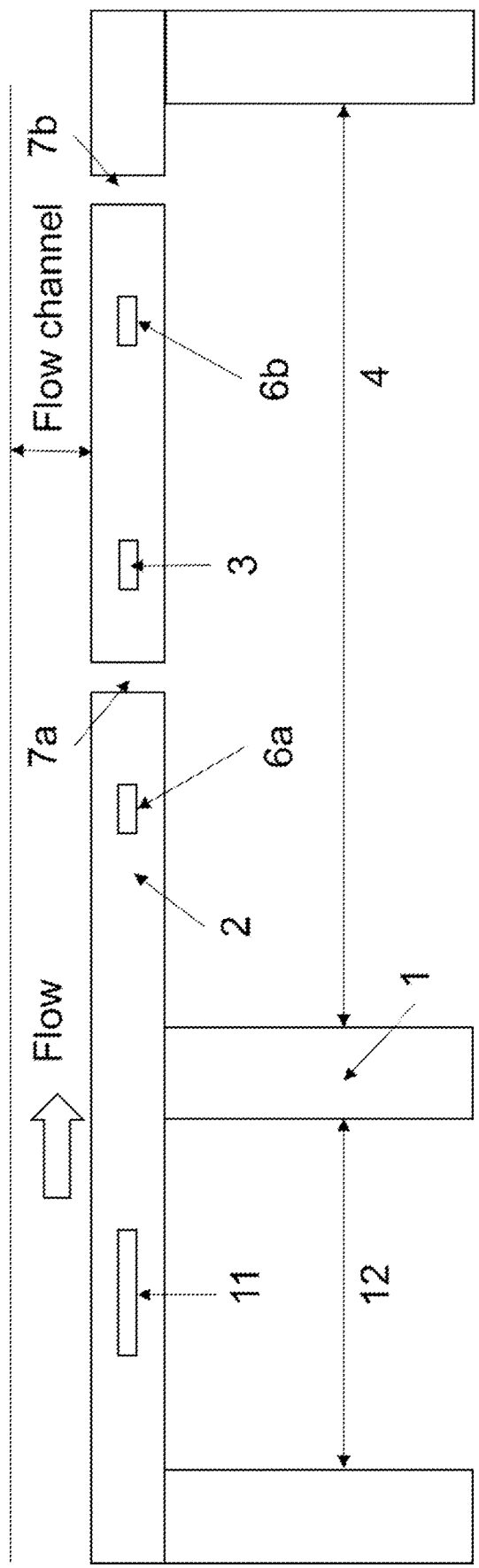
FIG. 31 illustrates schematically a cross-section of a sensor with an integrated additional heater for controlling or producing a temperature gradient, according to an alternative embodiment of the disclosure.

FIG. 31 illustrates schematically a cross-section of a sensor with an integrated additional heater for controlling or producing a temperature gradient, according to an alternative embodiment of the disclosure. FIG. 31 shows that an integrated microhotplate type with a specially designed heater could be used to create a temperature gradient, produce thermodiffusion and thus generate flow. The heater 11 could be powered up at high temperatures, optionally higher than those used for the heater of the sensor 3, to create and manipulate the flow. The integrated micro-hotplate using a heater 11 could be monolithically integrated with the flow/thermal conductivity sensor and use similar elements for the heater and the membrane. The membrane 12 could be adjacent to the sensor membrane 4 (as shown) or a single membrane could be used for both heaters (not shown). The flow could be created within a pre-defined channel formed as part of a manifold or a sensor housing.

Figure 32:
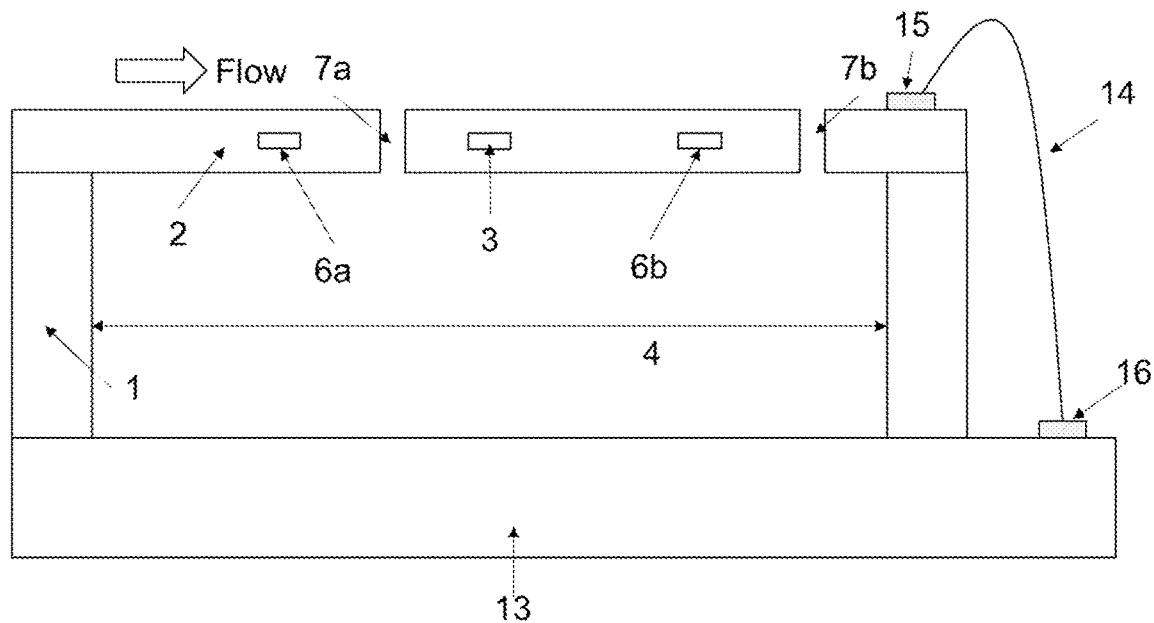
FIG. 32 illustrates schematically a cross-section of a sensor with an ASIC placed below the sensor, according to an alternative embodiment of the disclosure.

FIG. 32 illustrates schematically a cross-section of a sensor with an ASIC placed below the sensor, according to an alternative embodiment of the disclosure. FIG. 32 shows an arrangement where an ASIC 13 is placed below the flow/thermal conductivity sensor (using a stack die technique). The ASIC could be used to drive the sensor, read-out signals and process the signals. It could contain both analogue and digital blocks such as

- Current and voltage drives
- Current mirrors
- Voltage proportional to absolute temperature (VPTAT);
- Current proportional to absolute temperature (IPTAT);
- switches, multiplexer, decoder, filter, amplifier, analogue to digital converter, timing blocks, RF communication circuits, memories, and/or means for driving and reading out from the heating elements and/or temperature sensing elements; and/or
- means for electronically manipulating sensor signals; and/or
- means for enabling/disabling sensor elements.

In the die stack configuration shown in FIG. 32, the ASIC could be connected to the sensor via wires 14 using wire bonding and pads on the sensor 15 and on the ASIC 16.

Figure 33:
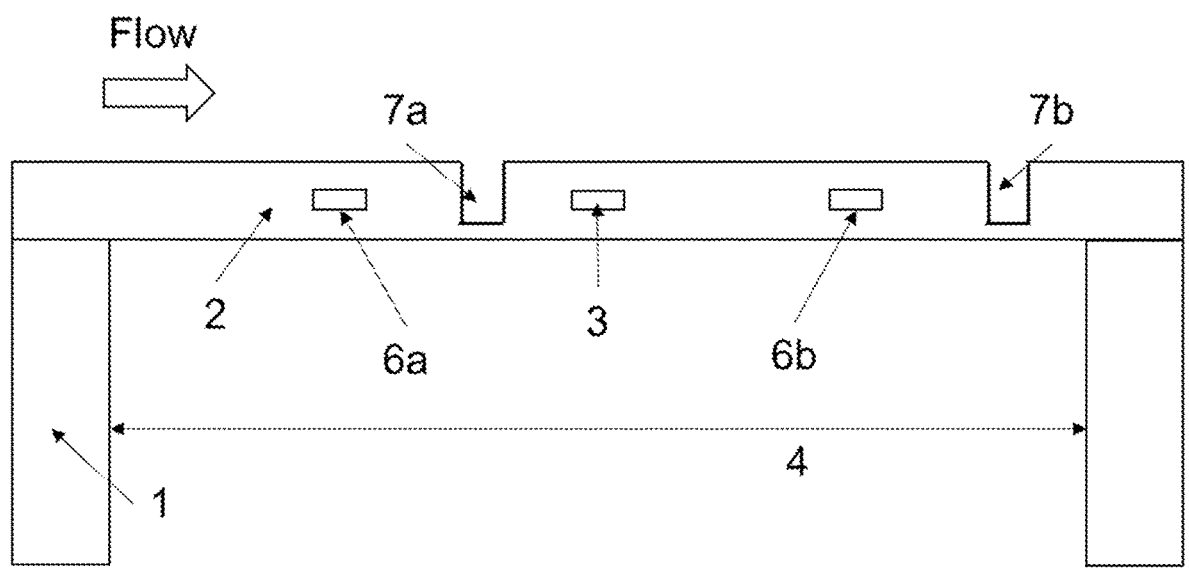
FIG. 33 illustrates schematically a cross-section of a sensor with trenches or partial recesses within the dielectric membrane, according to an alternative embodiment of the disclosure.

FIG. 33 illustrates schematically a cross-section of a sensor with trenches or partial recesses within the dielectric membrane, according to an alternative embodiment of the disclosure. FIG. 33 shows a similar structure to that shown in FIG. 6 where the holes do not need to connect the top and bottom surfaces of the membrane. 7a and 7b are shown as trenches or partial recesses formed from the top surface into the membrane. They provide a similar function to the holes shown in other embodiments, and partial recesses may be used instead of holes in any embodiment.

In effect in all the embodiments, a discontinuity could be referred to as a gap in the membrane from the top surface to the bottom surface (a hole). Though, not as effective in terms of the thermal performance, a discontinuity could also refer to a trench created from either the top or the bottom surface (if an upside-down membrane is used) without penetrating the other surface. The advantage of such partial holes (trenches or partial recesses) is that they impact less the mechanical strength of the membrane and in some cases they may be easier to be manufactured. Moreover such partial holes could be used to hermetically seal the bottom side of the membrane or allow no fluid penetration below the membrane.

Figure 34:
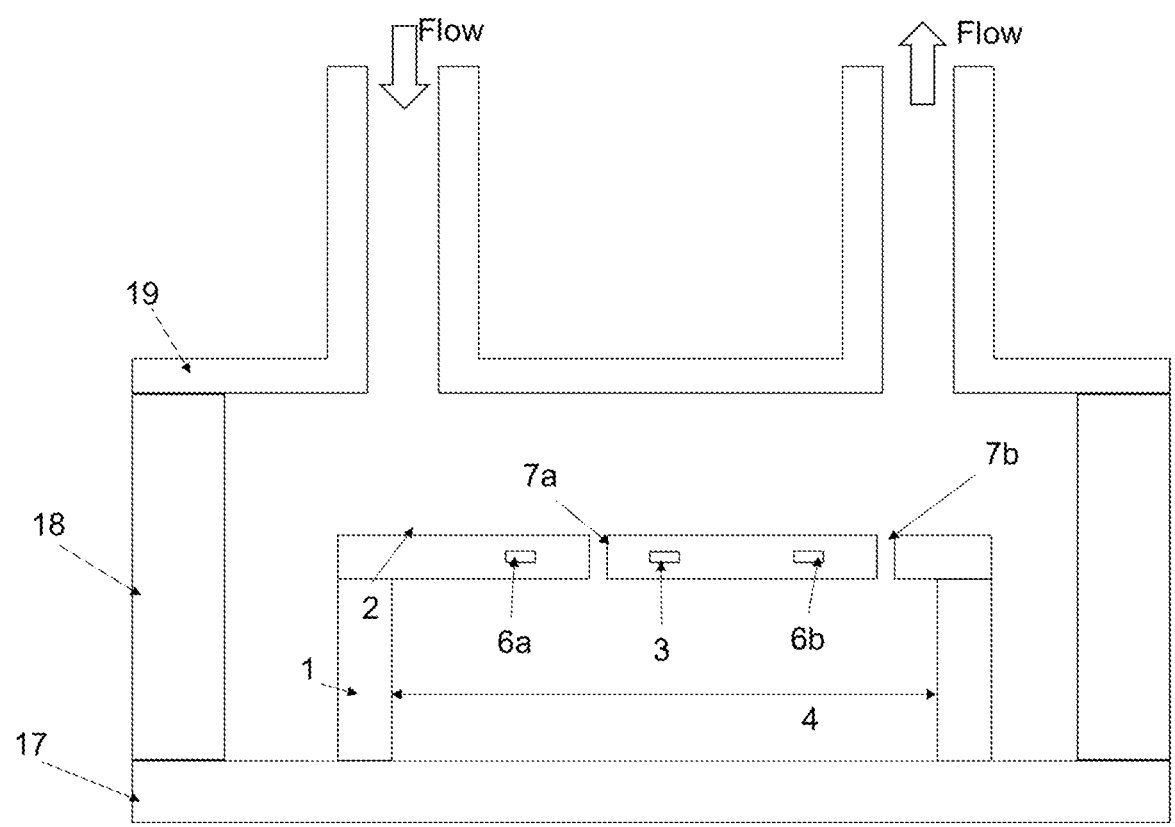
FIG. 34 illustrates schematically a cross-section of a sensor chip located within a flow sensor housing, according to an alternative embodiment of the disclosure.

FIG. 34 shows a sensor chip located within a flow sensor housing, according to an alternative embodiment of the disclosure. FIG. 34 shows the flow sensor chip inside a flow sensor housing, or miniaturised chamber such as a manifold. The housing includes a base 17 to which the chip is attached by an adhesive, die attach or solder. There are package walls 18, and a lid 19. The lid has an inlet and outlet to connect the flow. The base 17 and walls 18 could be made of a PCB (printed circuit board) type material, while the lid 97 could be moulded plastic. Other materials based on epoxies, resins are also possible.

The skilled person will understand that in the preceding description and appended claims, positional terms such as 'above', 'overlap', 'under', 'lateral', etc. are made with reference to conceptual illustrations of an device, such as those showing standard cross-sectional perspectives and those shown in the appended drawings. These terms are used for ease of reference but are not intended to be of limiting nature. These terms are therefore to be understood as referring to a device when in an orientation as shown in the accompanying drawings.

Although the disclosure has been described in terms of preferred embodiments as set forth above, it should be understood that these embodiments are illustrative only and that the claims are not limited to those embodiments. Those skilled in the art will be able to make modifications and alternatives in view of the disclosure which are contemplated as falling within the scope of the appended claims. Each feature disclosed or illustrated in the present specification may be incorporated in the disclosure, whether alone or in any appropriate combination with any other feature disclosed or illustrated herein.

The invention claimed is:

1. A sensor for measuring a property of a fluid, comprising:
 a semiconductor substrate comprising an etched portion;
 a dielectric region located on the semiconductor substrate, wherein the dielectric region comprises at least one dielectric membrane located over the etched portion of the semiconductor substrate;
 a heating element located within the dielectric membrane; and
 a pair of temperature sensing elements having a first temperature sensing element of the pair of temperature sensing elements and a second temperature sensing element of the pair of temperature sensing elements respectively located on opposing sides of the heating element, and wherein the pair of temperature sensing elements are located within the dielectric membrane,
 wherein the dielectric membrane comprises at least one recessed region between the heating element and an edge of the dielectric membrane so that the dielectric membrane is arranged asymmetrically about an axis defined by the heating element such that there is a greater recessed volume between the heating element and the first temperature sensing element of the pair of temperature sensing elements than between the heating element and the second temperature sensing element of the pair of temperature sensing elements, such that the at least one recessed region introduces a temperature difference between the first temperature sensing element of the pair of temperature sensing elements and the second temperature sensing element of the pair of temperature sensing elements due to differences in heat conduction through the dielectric membrane caused by the asymmetrically arranged dielectric membrane so that a differential signal between the pair of temperature sensing elements is indicative of composition or concentration of the fluid based on a thermal conductivity of the fluid.

2. The sensor according to claim 1, wherein the heating element is configured to operate as a temperature sensing element.

3. The sensor according to claim 1, wherein the at least one recessed region comprises or is made of one or more holes.

4. The sensor according to claim 3, wherein at least one of the one or more holes comprises an elongate slot extending towards opposite edges of the dielectric membrane.

5. The sensor according to claim 3, wherein the one or more holes comprises an array of perforations.

6. The sensor according to claim 1, wherein at least one recessed region is partially recessed within the dielectric membrane.

7. The sensor according to claim 1, wherein at least one of the pair of temperature sensing elements is configured to measure a temperature difference across the heating element, and/or
 wherein at least one of the pair of temperature sensing elements is configured to measure a temperature difference between the dielectric membrane and the dielectric region above the semiconductor substrate.

8. The sensor according to claim 1, wherein the at least one recessed region comprises a first recessed region and a second recessed region, the first recessed region is located between the first of the temperature sensing elements and the heater and the second recessed region is located between the second of the temperature sensing elements and an opposing edge of the dielectric membrane.

9. The sensor according to claim 1, wherein the one or more temperature sensing elements comprise resistive temperature detectors, diodes, or thermopiles.

10. The sensor according to claim 1, wherein the pair of temperature sensing elements is a first pair of temperature sensing elements and the sensor comprises another pair of temperature sensing elements being a second pair of temperature sensing elements, and
 wherein a differential signal between the second pair of temperature sensing elements is configured to measure a flow property of the fluid.

11. The sensor according to claim 1, wherein the axis defined by the heating element is perpendicular to a direction of flow of the fluid through the sensor.

12. The sensor according to claim 1, comprising a further heating element extending in a direction parallel to the direction of flow of the fluid through the sensor.

13. The sensor according to claim 12, further comprising another pair of temperature sensing elements configured to measure a differential signal across the further heating element.

14. The sensor according to claim 1, wherein the dielectric membrane is circular and wherein at least one of the recessed regions has an arc shape.

15. The sensor according to claim 1, further comprising:
 a flow mechanism configured to provide or control flow of the fluid through the sensor, and wherein the flow mechanism comprises at least one additional heater configured to produce a temperature gradient across the sensor.

16. A flow sensing device comprising:
 a flow sensor housing; and
 the sensor according to claim 1 located within the flow sensor housing.

17. The sensor according to claim 1, wherein the sensor is further configured to operate as a flow sensor to measure any of a flow rate, mass flow rate or volume flow rate, as well as composition or concentration.

18. The sensor according to claim 1, further comprising an application specific integrated circuit (ASIC) coupled to the sensor.

19. A method of manufacturing a sensor for measuring a property of a fluid, the method comprising:
 forming at least one dielectric membrane on a semiconductor substrate comprising an etched portion, wherein the dielectric membrane is over an area of the etched portion of the semiconductor substrate;
 forming a heating element within the dielectric membrane;
 forming a pair of temperature sensing elements having a first temperature sensing element of the pair of temperature sensing elements and a second temperature sensing element of the pair of temperature sensing elements respectively located on opposing sides of the heating element, and wherein the pair of temperature sensing elements are located within the dielectric membrane,
 forming at least one recessed region within the dielectric membrane and located between the heating element and an edge of the dielectric membrane so that the dielectric membrane is arranged asymmetrically about an axis defined by the heating element such that there is a greater recessed volume between the heating element and the first temperature sensing element of the pair of temperature sensing elements than between the heating element and the second temperature sensing element of the pair of temperature sensing elements, such that the at least one recessed region introduces a temperature difference between the first temperature sensing element of the pair of temperature sensing elements and the second temperature sensing element of the pair of temperature sensing elements due to differences in heat conduction through the dielectric membrane caused by the asymmetrically arranged dielectric membrane so that a differential signal between the pair of temperature sensing elements is indicative of composition or concentration of the fluid based on a thermal conductivity of the fluid.

\* \* \* \* \*